United States Patent
Mangiardi et al.

(10) Patent No.: US 7,637,934 B2
(45) Date of Patent: Dec. 29, 2009

(54) MEDICAL APPLIANCE OPTICAL DELIVERY AND DEPLOYMENT APPARATUS AND METHOD

(75) Inventors: Eric K. Mangiardi, Charlotte, NC (US); Ulf R. Borg, Cornelius, NC (US); Jason M. Reynolds, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 10/404,197

(22) Filed: Mar. 31, 2003

(65) Prior Publication Data

US 2004/0193243 A1    Sep. 30, 2004

(51) Int. Cl.
*A61F 2/06* (2006.01)
(52) U.S. Cl. .................. 623/1.12; 623/1.11; 606/108
(58) Field of Classification Search .................. None
See application file for complete search history.

(56) References Cited

U.S. PATENT DOCUMENTS

| | | | |
|---|---|---|---|
| 3,196,876 | A | 7/1965 | Miller |
| 4,343,048 | A | 8/1982 | Ross et al. |
| 4,606,330 | A | 8/1986 | Bonnet |
| 4,665,906 | A | 5/1987 | Jervis |
| 4,680,031 | A | 7/1987 | Alonso |
| 4,733,665 | A | 3/1988 | Palmaz |
| 4,739,762 | A | 4/1988 | Palmaz |
| 4,820,262 | A | 4/1989 | Finney |
| 4,893,623 | A | 1/1990 | Rosenbluth |
| 5,019,085 | A | 5/1991 | Hillstead |
| 5,032,128 | A | 7/1991 | Alonso |
| 5,067,957 | A | 11/1991 | Jervis |
| 5,073,694 | A | 12/1991 | Tessier et al. |
| 5,102,417 | A | 4/1992 | Palmaz |

(Continued)

FOREIGN PATENT DOCUMENTS

DE    199 06 956 A1    8/2000

(Continued)

OTHER PUBLICATIONS

Supplemental Partial European Search Report mailed Mar. 19, 2007 for PCT/US2004/009679 (Filed Mar. 30, 2004).

(Continued)

*Primary Examiner*—Corrine M McDermott
*Assistant Examiner*—Christopher D Prone
(74) *Attorney, Agent, or Firm*—Alston & Bird LLP

(57) ABSTRACT

Embodiments of the present invention are directed to devices for allowing a user to deploy a stent in an anatomical lumen of a patient. For example, one embodiment is directed to a device including a longitudinally extending inner tubular member and a longitudinally extending outer tubular member that are longitudinally and axially displaceable relative to one another. The outer tubular member includes at least one longitudinally extending channel formed between the exterior and interior diameter of the outer tubular member. In addition, the device includes a handle configured to displace the outer tubular member and inner tubular member relative to each other in response to user intervention and a stop configured to coaxially engage the handle to form a safety mechanism. Displaceability of the outer tubular member and inner tubular member relative to each other is limited by the safety mechanism to a predetermined threshold.

108 Claims, 12 Drawing Sheets

U.S. PATENT DOCUMENTS

| | | | |
|---|---|---|---|
| 5,104,404 A | 4/1992 | Wolff | |
| 5,159,920 A | 11/1992 | Condon et al. | |
| 5,190,546 A | 3/1993 | Jervis | |
| 5,195,984 A | 3/1993 | Schatz | |
| 5,249,585 A | 10/1993 | Turner et al. | |
| 5,292,331 A | 3/1994 | Boneau | |
| 5,320,617 A | 6/1994 | Leach | |
| 5,345,057 A | 9/1994 | Muller | |
| 5,354,309 A | 10/1994 | Schnepp-Pesch et al. | |
| 5,356,423 A | 10/1994 | Tihon et al. | |
| 5,383,892 A | 1/1995 | Cardon et al. | |
| 5,409,453 A | 4/1995 | Lundquist et al. | |
| 5,421,955 A | 6/1995 | Lau et al. | |
| 5,433,723 A * | 7/1995 | Lindenberg et al. | 606/198 |
| 5,443,498 A | 8/1995 | Fontaine | |
| 5,449,373 A | 9/1995 | Pinchasik et al. | |
| 5,514,093 A | 5/1996 | Ellis et al. | |
| 5,514,154 A | 5/1996 | Lau et al. | |
| 5,534,287 A | 7/1996 | Lukic | |
| 5,549,644 A | 8/1996 | Lundquist et al. | |
| 5,588,949 A | 12/1996 | Taylor et al. | |
| 5,591,157 A | 1/1997 | Hennings et al. | |
| 5,591,197 A | 1/1997 | Orth et al. | |
| 5,593,442 A | 1/1997 | Klein | |
| 5,597,378 A | 1/1997 | Jervis | |
| 5,601,591 A | 2/1997 | Edwards et al. | |
| 5,601,593 A | 2/1997 | Freitag | |
| 5,603,698 A * | 2/1997 | Roberts et al. | 604/104 |
| 5,609,629 A | 3/1997 | Fearnot et al. | |
| 5,618,300 A | 4/1997 | Marin | |
| 5,628,788 A | 5/1997 | Pinchuk | |
| 5,643,312 A | 7/1997 | Fischell et al. | |
| 5,662,713 A | 9/1997 | Andersen et al. | |
| 5,667,522 A | 9/1997 | Flomenblit et al. | |
| 5,681,346 A | 10/1997 | Orth et al. | |
| 5,690,644 A | 11/1997 | Yurek et al. | |
| 5,695,499 A | 12/1997 | Helgerson et al. | |
| 5,702,418 A | 12/1997 | Ravenscroft | |
| 5,707,386 A | 1/1998 | Schnepp-Pesch et al. | |
| 5,713,949 A | 2/1998 | Jayaraman | |
| 5,716,393 A | 2/1998 | Lindenberg et al. | |
| 5,733,303 A | 3/1998 | Israel et al. | |
| 5,741,333 A | 4/1998 | Frid | |
| 5,746,692 A | 5/1998 | Bacich et al. | |
| 5,755,776 A | 5/1998 | Al-Saadon | |
| 5,759,192 A | 6/1998 | Saunders | |
| 5,766,238 A | 6/1998 | Lau et al. | |
| 5,776,161 A | 7/1998 | Globerman | |
| 5,780,807 A | 7/1998 | Saunders | |
| 5,782,838 A | 7/1998 | Beyar et al. | |
| 5,803,080 A | 9/1998 | Freitag | |
| 5,807,404 A | 9/1998 | Richter | |
| 5,814,063 A | 9/1998 | Freitag | |
| 5,817,102 A | 10/1998 | Johnson et al. | |
| 5,824,042 A | 10/1998 | Lombardi et al. | |
| 5,824,058 A | 10/1998 | Ravenscroft et al. | |
| 5,830,179 A * | 11/1998 | Mikus et al. | 604/517 |
| 5,833,694 A | 11/1998 | Poncet | |
| 5,836,966 A | 11/1998 | St. Germain | |
| 5,837,313 A | 11/1998 | Ding et al. | |
| 5,843,120 A | 12/1998 | Israel et al. | |
| 5,860,999 A | 1/1999 | Schnepp-Pesch et al. | |
| 5,873,904 A | 2/1999 | Ragheb et al. | |
| 5,876,445 A | 3/1999 | Andersen et al. | |
| 5,876,448 A | 3/1999 | Thompson et al. | |
| 5,876,449 A | 3/1999 | Starck et al. | |
| 5,879,370 A | 3/1999 | Fischell et al. | |
| 5,902,333 A | 5/1999 | Roberts et al. | |
| 5,902,475 A | 5/1999 | Trozera et al. | |
| 5,911,732 A | 6/1999 | Hojeibane | |
| 5,922,020 A | 7/1999 | Klein et al. | |
| 5,922,393 A | 7/1999 | Jayaraman | |
| 5,935,162 A | 8/1999 | Dang | |
| 5,954,729 A | 9/1999 | Bachmann | |
| 5,968,052 A | 10/1999 | Sullivan, III et al. | |
| 5,968,070 A | 10/1999 | Bley et al. | |
| 5,968,091 A | 10/1999 | Pinchuk et al. | |
| 5,972,018 A | 10/1999 | Israel et al. | |
| 5,980,552 A | 11/1999 | Pinchasik et al. | |
| 5,984,964 A | 11/1999 | Roberts et al. | |
| 6,017,365 A | 1/2000 | Von Oepen | |
| 6,019,778 A | 2/2000 | Wilson et al. | |
| 6,022,371 A | 2/2000 | Killion | |
| 6,033,435 A | 3/2000 | Penn et al. | |
| 6,042,597 A | 3/2000 | Kveen et al. | |
| 6,048,361 A | 4/2000 | Von Oepen | |
| 6,051,021 A | 4/2000 | Frid | |
| 6,053,941 A | 4/2000 | Lindenberg et al. | |
| 6,056,775 A | 5/2000 | Borghi et al. | |
| 6,059,811 A | 5/2000 | Pinchasik et al. | |
| 6,086,528 A | 7/2000 | Adair | |
| 6,096,070 A | 8/2000 | Ragheb et al. | |
| 6,099,560 A | 8/2000 | Penn et al. | |
| 6,131,266 A | 10/2000 | Saunders | |
| 6,132,461 A | 10/2000 | Thompson | |
| 6,136,006 A | 10/2000 | Johnson et al. | |
| 6,146,403 A | 11/2000 | St. Germain | |
| 6,146,416 A | 11/2000 | Andersen et al. | |
| 6,156,035 A | 12/2000 | Songer | |
| 6,156,052 A | 12/2000 | Richter et al. | |
| 6,162,231 A | 12/2000 | Mikus et al. | |
| 6,174,329 B1 | 1/2001 | Callol et al. | |
| 6,179,867 B1 | 1/2001 | Cox | |
| 6,203,550 B1 | 3/2001 | Olson | |
| 6,203,568 B1 | 3/2001 | Lombardi et al. | |
| 6,217,608 B1 | 4/2001 | Penn et al. | |
| 6,238,430 B1 | 5/2001 | Klumb et al. | |
| 6,270,524 B1 | 8/2001 | Kim | |
| 6,299,622 B1 | 10/2001 | Snow et al. | |
| 6,302,906 B1 | 10/2001 | Goicoechea et al. | |
| 6,306,141 B1 | 10/2001 | Jervis | |
| 6,315,794 B1 | 11/2001 | Richter | |
| 6,322,586 B1 | 11/2001 | Monroe et al. | |
| 6,325,790 B1 | 12/2001 | Trotta | |
| 6,355,063 B1 | 3/2002 | Calcote | |
| 6,361,557 B1 | 3/2002 | Gittings et al. | |
| 6,369,355 B1 | 4/2002 | Saunders | |
| 6,375,676 B1 | 4/2002 | Cox | |
| 6,380,457 B1 | 4/2002 | Yurek et al. | |
| 6,423,084 B1 | 7/2002 | St. Germain | |
| 6,428,538 B1 | 8/2002 | Blewett et al. | |
| 6,428,570 B1 | 8/2002 | Globerman | |
| 6,440,162 B1 | 8/2002 | Cox et al. | |
| 6,443,982 B1 | 9/2002 | Israel et al. | |
| 6,451,025 B1 | 9/2002 | Jervis | |
| 6,454,789 B1 | 9/2002 | Chen et al. | |
| 6,461,381 B2 | 10/2002 | Israel et al. | |
| 6,464,720 B2 | 10/2002 | Boatman et al. | |
| 6,464,722 B2 | 10/2002 | Israel et al. | |
| 6,475,234 B1 | 11/2002 | Richter et al. | |
| 6,488,697 B1 | 12/2002 | Ariura et al. | |
| 6,508,834 B1 | 1/2003 | Pinchasik et al. | |
| 6,514,245 B1 | 2/2003 | Williams et al. | |
| 6,514,285 B1 | 2/2003 | Pinchasik | |
| 6,517,569 B2 | 2/2003 | Mikus et al. | |
| 6,533,805 B1 | 3/2003 | Jervis | |
| 6,540,777 B2 | 4/2003 | Stenzel | |
| 6,569,085 B2 | 5/2003 | Kortenbach et al. | |
| 6,569,194 B1 | 5/2003 | Pelton | |
| 6,572,646 B1 | 6/2003 | Boylan et al. | |
| 6,589,276 B2 | 7/2003 | Pinchasik et al. | |
| 6,607,551 B1 | 8/2003 | Sullivan et al. | |
| 6,613,078 B1 | 9/2003 | Barone | |
| 6,620,193 B1 | 9/2003 | Lau et al. | |

| Patent No. | Date | Inventor |
|---|---|---|
| 6,623,491 B2 | 9/2003 | Thompson |
| 6,626,902 B1 * | 9/2003 | Kucharczyk et al. .......... 606/41 |
| 6,635,084 B2 | 10/2003 | Israel et al. |
| 6,638,293 B1 | 10/2003 | Makower et al. |
| 6,638,300 B1 | 10/2003 | Frantzen |
| 6,638,302 B1 | 10/2003 | Curcio et al. |
| 6,641,607 B1 | 11/2003 | Hossainy et al. |
| 6,641,608 B1 | 11/2003 | Pulnev |
| 6,641,609 B2 | 11/2003 | Globerman |
| 6,641,611 B2 | 11/2003 | Jayaraman |
| 6,645,240 B2 | 11/2003 | Yee |
| 6,645,242 B1 | 11/2003 | Quinn |
| 6,652,573 B2 | 11/2003 | von Oepen |
| 6,652,575 B2 | 11/2003 | Wang |
| 6,653,426 B2 | 11/2003 | Alvarado et al. |
| 6,656,201 B2 | 12/2003 | Ferrera et al. |
| 6,656,211 B1 | 12/2003 | DiCaprio |
| 6,656,214 B1 | 12/2003 | Fogarty et al. |
| 6,656,217 B1 | 12/2003 | Herzog, Jr. et al. |
| 6,656,351 B2 | 12/2003 | Boyle |
| 6,660,030 B2 | 12/2003 | Shaolian et al. |
| 6,660,034 B1 | 12/2003 | Mandrusov et al. |
| 6,660,827 B1 | 12/2003 | Loomis et al. |
| 6,663,660 B2 | 12/2003 | Dusbabek et al. |
| 6,663,664 B1 | 12/2003 | Pacetti |
| 6,663,880 B1 | 12/2003 | Roorda et al. |
| 6,664,335 B2 | 12/2003 | Krishnan |
| 6,666,881 B1 | 12/2003 | Richter et al. |
| 6,666,884 B1 | 12/2003 | Webster |
| 6,669,716 B1 | 12/2003 | Gilson et al. |
| 6,669,718 B2 | 12/2003 | Besselink |
| 6,669,720 B1 | 12/2003 | Pierce |
| 6,669,721 B1 | 12/2003 | Bose et al. |
| 6,669,722 B2 | 12/2003 | Chen et al. |
| 6,669,723 B2 | 12/2003 | Killion et al. |
| 6,673,101 B1 | 1/2004 | Fitzgerald et al. |
| 6,673,102 B1 | 1/2004 | Vonesh et al. |
| 6,673,103 B1 | 1/2004 | Golds et al. |
| 6,673,104 B2 | 1/2004 | Barry |
| 6,673,105 B1 | 1/2004 | Chen |
| 6,673,107 B1 | 1/2004 | Brandt et al. |
| 6,673,154 B1 | 1/2004 | Pacetti et al. |
| 6,676,692 B2 | 1/2004 | Rabkin et al. |
| 6,676,693 B1 | 1/2004 | Belding et al. |
| 6,676,697 B1 | 1/2004 | Richter |
| 6,679,910 B1 | 1/2004 | Granada |
| 6,679,911 B2 | 1/2004 | Burgermeister |
| 6,685,736 B1 | 2/2004 | White et al. |
| 6,685,745 B2 | 2/2004 | Reever |
| 6,689,157 B2 | 2/2004 | Madrid et al. |
| 6,689,158 B1 | 2/2004 | White et al. |
| 6,692,483 B2 | 2/2004 | Vardi et al. |
| 6,692,522 B1 | 2/2004 | Richter |
| 6,695,809 B1 | 2/2004 | Lee |
| 6,695,812 B2 | 2/2004 | Estrada et al. |
| 6,695,833 B1 | 2/2004 | Frantzen |
| 6,695,862 B2 | 2/2004 | Cox et al. |
| 6,695,876 B1 | 2/2004 | Marotta et al. |
| 6,699,274 B2 | 3/2004 | Stinson |
| 6,699,276 B2 | 3/2004 | Sogard et al. |
| 6,699,277 B1 | 3/2004 | Freidberg et al. |
| 6,702,849 B1 | 3/2004 | Dutta et al. |
| 6,702,850 B1 | 3/2004 | Byun et al. |
| 6,706,061 B1 | 3/2004 | Fischell et al. |
| 6,706,062 B1 | 3/2004 | Vardi et al. |
| 6,709,440 B2 | 3/2004 | Callol et al. |
| 6,709,451 B1 | 3/2004 | Noble et al. |
| 6,712,846 B1 | 3/2004 | Kraus et al. |
| 6,716,240 B2 | 4/2004 | Fischell et al. |
| 6,719,782 B1 | 4/2004 | Chuter |
| 6,719,991 B2 | 4/2004 | Darouiche et al. |
| 6,723,071 B2 | 4/2004 | Gerdts et al. |
| 6,723,113 B1 | 4/2004 | Shkolnik |
| 6,723,120 B2 | 4/2004 | Yan |
| 6,723,121 B1 | 4/2004 | Zhong |
| 6,723,373 B1 | 4/2004 | Narayanan et al. |
| 6,726,712 B1 | 4/2004 | Raeder-Devens et al. |
| 6,730,064 B2 | 5/2004 | Ragheb et al. |
| 6,730,116 B1 | 5/2004 | Wolinsky et al. |
| 6,730,117 B1 | 5/2004 | Tseng et al. |
| 6,733,521 B2 | 5/2004 | Chobotov et al. |
| 6,733,523 B2 | 5/2004 | Shaolian et al. |
| 6,733,524 B2 | 5/2004 | Tseng et al. |
| 6,736,828 B1 | 5/2004 | Adams et al. |
| 6,736,838 B1 | 5/2004 | Richter |
| 6,740,113 B2 | 5/2004 | Vrba |
| 6,740,114 B2 | 5/2004 | Burgermeister |
| 6,740,115 B2 | 5/2004 | Lombardi et al. |
| 6,743,219 B1 | 6/2004 | Dwyer et al. |
| 6,746,423 B1 | 6/2004 | Wantink |
| 6,746,475 B1 | 6/2004 | Rivelli, Jr. |
| 6,746,476 B1 | 6/2004 | Hojeibane |
| 6,746,479 B2 | 6/2004 | Ehr et al. |
| 6,746,482 B2 | 6/2004 | Ung-Chhun |
| 6,749,627 B2 | 6/2004 | Thompson et al. |
| 6,749,629 B1 | 6/2004 | Hong et al. |
| 6,752,819 B1 | 6/2004 | Brady et al. |
| 6,752,825 B2 | 6/2004 | Eskuri |
| 6,752,826 B2 | 6/2004 | Holloway et al. |
| 6,752,829 B2 | 6/2004 | Kocur et al. |
| 6,753,071 B1 | 6/2004 | Pacetti |
| 6,755,855 B2 | 6/2004 | Yurek et al. |
| 6,756,007 B2 | 6/2004 | Pletzer et al. |
| 6,758,858 B2 | 7/2004 | McCrea et al. |
| 6,758,859 B1 | 7/2004 | Dang et al. |
| 6,761,703 B2 | 7/2004 | Miller et al. |
| 6,761,708 B1 | 7/2004 | Chiu et al. |
| 6,761,731 B2 | 7/2004 | Majercak |
| 6,761,733 B2 | 7/2004 | Chobotov et al. |
| 6,764,505 B1 | 7/2004 | Hossainy et al. |
| 6,764,506 B2 | 7/2004 | Roubin et al. |
| 6,764,507 B2 | 7/2004 | Shanley et al. |
| 6,764,519 B2 | 7/2004 | Whitmore, III |
| 6,770,086 B1 | 8/2004 | Girton |
| 6,770,088 B1 | 8/2004 | Jang |
| 6,770,091 B2 | 8/2004 | Richter et al. |
| 6,773,446 B1 | 8/2004 | Dwyer et al. |
| 6,773,447 B2 | 8/2004 | Laguna |
| 6,773,448 B2 | 8/2004 | Kusleika et al. |
| 6,774,157 B2 | 8/2004 | DelMain |
| 6,774,278 B1 | 8/2004 | Ragheb et al. |
| 6,776,792 B1 | 8/2004 | Yan et al. |
| 6,776,793 B2 | 8/2004 | Brown et al. |
| 6,776,795 B2 | 8/2004 | Pelton |
| 6,776,796 B2 | 8/2004 | Falotico et al. |
| 6,780,182 B2 | 8/2004 | Bowman et al. |
| 6,780,199 B2 | 8/2004 | Solar et al. |
| 6,786,918 B1 | 9/2004 | Krivoruchko et al. |
| 6,786,929 B2 | 9/2004 | Gambale et al. |
| 6,790,220 B2 | 9/2004 | Morris et al. |
| 6,790,222 B2 | 9/2004 | Kugler et al. |
| 6,790,223 B2 | 9/2004 | Reever |
| 6,790,227 B2 | 9/2004 | Burgermeister |
| 6,790,228 B2 | 9/2004 | Hossainy et al. |
| 6,796,997 B1 | 9/2004 | Penn et al. |
| 6,797,217 B2 | 9/2004 | McCrea et al. |
| 6,800,081 B2 | 10/2004 | Parodi |
| 6,800,089 B1 | 10/2004 | Wang |
| 6,802,846 B2 | 10/2004 | Hauschild et al. |
| 6,802,849 B2 | 10/2004 | Blaeser et al. |
| 6,802,859 B1 | 10/2004 | Pazienza et al. |
| 6,805,702 B1 | 10/2004 | Chen et al. |
| 6,805,703 B2 | 10/2004 | McMorrow |
| 6,805,704 B1 | 10/2004 | Hoyns |
| 6,805,705 B2 | 10/2004 | Hong et al. |
| 6,805,706 B2 | 10/2004 | Solovay et al. |

| | | | |
|---|---|---|---|
| 6,805,707 B1 | 10/2004 | Hong et al. | |
| 6,805,709 B1 | 10/2004 | Schaldach et al. | |
| 6,805,898 B1 | 10/2004 | Wu et al. | |
| 6,808,529 B2 | 10/2004 | Fulkerson | |
| 6,808,533 B1 | 10/2004 | Goodwin et al. | |
| 6,843,802 B1 | 1/2005 | Villalobos et al. | |
| 6,860,898 B2 | 3/2005 | Stack et al. | |
| 6,899,727 B2 | 5/2005 | Armstrong et al. | |
| 6,911,039 B2 | 6/2005 | Shiu et al. | |
| 6,942,674 B2 | 9/2005 | Belef et al. | |
| 6,953,475 B2 | 10/2005 | Shaolian et al. | |
| 6,972,054 B2 | 12/2005 | Kerrigan | |
| 6,984,244 B2 | 1/2006 | Perez et al. | |
| 6,989,024 B2 | 1/2006 | Herbert et al. | |
| 7,011,675 B2 | 3/2006 | Hemerick et al. | |
| 2001/0016767 A1 | 8/2001 | Wilson et al. | |
| 2001/0016768 A1 | 8/2001 | Wilson et al. | |
| 2001/0027339 A1 | 10/2001 | Boatman et al. | |
| 2001/0037138 A1 | 11/2001 | Wilston et al. | |
| 2002/0002396 A1 | 1/2002 | Fulkerson | |
| 2002/0042650 A1 | 4/2002 | Vardi et al. | |
| 2002/0111672 A1 | 8/2002 | Kim et al. | |
| 2002/0156524 A1 | 10/2002 | Ehr et al. | |
| 2002/0161425 A1 | 10/2002 | Hemerick et al. | |
| 2002/0183763 A1 | 12/2002 | Callot et al. | |
| 2002/0183831 A1 | 12/2002 | Rolando et al. | |
| 2002/0183832 A1 | 12/2002 | Penn et al. | |
| 2002/0193866 A1 | 12/2002 | Saunders | |
| 2002/0198593 A1 | 12/2002 | Gomez et al. | |
| 2003/0004567 A1 | 1/2003 | Boyle et al. | |
| 2003/0028240 A1 | 2/2003 | Nolting et al. | |
| 2003/0036793 A1 | 2/2003 | Richter et al. | |
| 2003/0045925 A1 | 3/2003 | Jayaraman | |
| 2003/0050690 A1 | 3/2003 | Kveen et al. | |
| 2003/0074045 A1 | 4/2003 | Buzzard et al. | |
| 2003/0077310 A1 | 4/2003 | Pathak et al. | |
| 2003/0083734 A1 | 5/2003 | Friedrich et al. | |
| 2003/0105511 A1 | 6/2003 | Welsh et al. | |
| 2003/0105513 A1 | 6/2003 | Moriuchi et al. | |
| 2003/0114919 A1 | 6/2003 | McQuiston et al. | |
| 2003/0125799 A1 | 7/2003 | Limon | |
| 2003/0139796 A1 | 7/2003 | Sequin et al. | |
| 2003/0139803 A1 | 7/2003 | Sequin et al. | |
| 2003/0144671 A1 | 7/2003 | Brooks et al. | |
| 2003/0144726 A1 | 7/2003 | Majercak et al. | |
| 2003/0144731 A1 | 7/2003 | Wolinsky et al. | |
| 2003/0149469 A1 | 8/2003 | Wolinsky et al. | |
| 2003/0158596 A1 | 8/2003 | Ikeuchi et al. | |
| 2004/0006380 A1 | 1/2004 | Buck et al. | |
| 2004/0093056 A1 | 5/2004 | Johnson et al. | |

FOREIGN PATENT DOCUMENTS

| | | |
|---|---|---|
| DE | 199 37 638 A1 | 5/2001 |
| EP | 0 350 302 | 1/1990 |
| EP | 0 364 420 A1 | 4/1990 |
| EP | 0 378 151 A2 | 7/1990 |
| EP | 0 516 189 A1 | 12/1992 |
| EP | 0 540 290 A2 | 5/1993 |
| EP | 0 797 963 A2 | 1/1997 |
| EP | 0 792 627 A2 | 3/1997 |
| EP | 0 945 107 A2 | 1/1999 |
| EP | 1 093 771 A2 | 4/2001 |
| EP | 1 208 814 A2 | 9/2001 |
| EP | 1 290 984 A2 | 12/2003 |
| JP | 2001-299932 | 10/2001 |
| JP | 2002-102251 | 4/2002 |
| JP | 2002-345971 | 12/2002 |
| WO | WO 91/13384 | 9/1991 |
| WO | WO 92/11824 | 7/1992 |
| WO | WO 93/22986 | 11/1993 |
| WO | WO 94/04096 | 3/1994 |
| WO | WO 94/21196 | 9/1994 |
| WO | WO 97/07751 | 3/1997 |
| WO | WO 97/10011 | 3/1997 |
| WO | WO 97/14456 | 4/1997 |
| WO | WO 97/40739 | 11/1997 |
| WO | WO 98/20811 | 5/1998 |
| WO | WO 99/49812 | 10/1999 |
| WO | WO 99/62430 | 12/1999 |
| WO | WO 00/09041 | 2/2000 |
| WO | WO 00/45742 | 8/2000 |
| WO | WO 01/76508 A2 | 10/2001 |
| WO | WO 02/19948 A2 | 3/2002 |
| WO | WO 02/083038 A2 | 10/2002 |

OTHER PUBLICATIONS

Related U.S. Appl. No. 11/357,366, filed Feb. 17, 2006, entitled "Medical Appliance Delivery Apparatus and Method of Use".

Office Action from related U.S. Appl. No. 11/357,366, mailed Feb. 13, 2007.

Office Action from related U.S. Appl. No. 11/357,366, mailed Jul. 12, 2007.

Office Action from related U.S. Appl. No. 11/357,366, mailed Mar. 26, 2008.

* cited by examiner

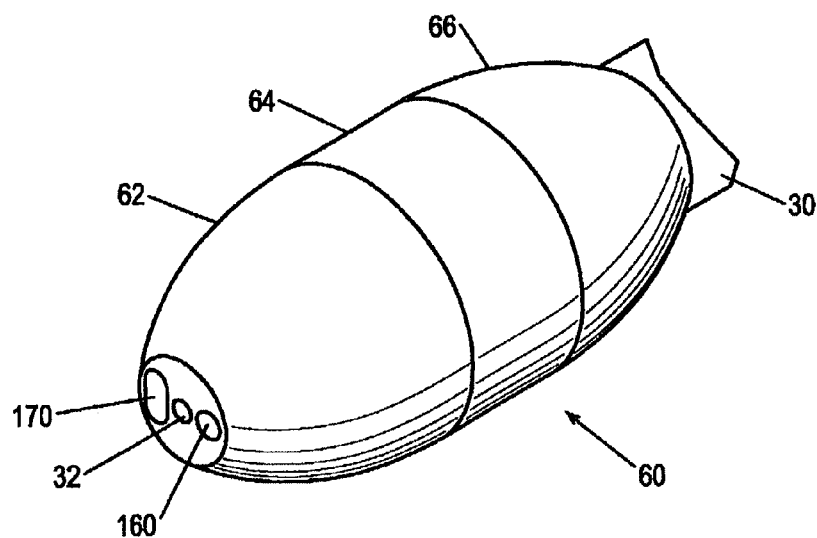
Fig. 5
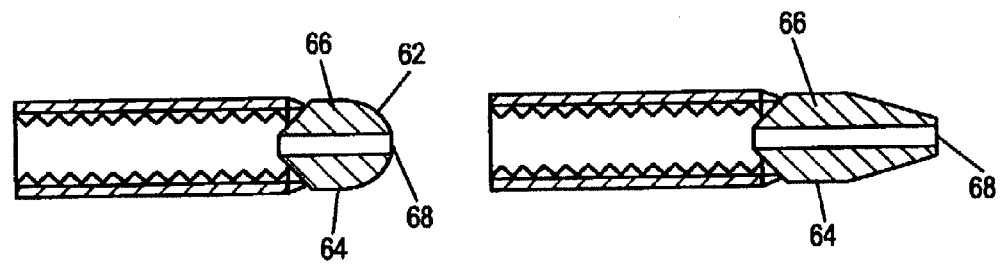
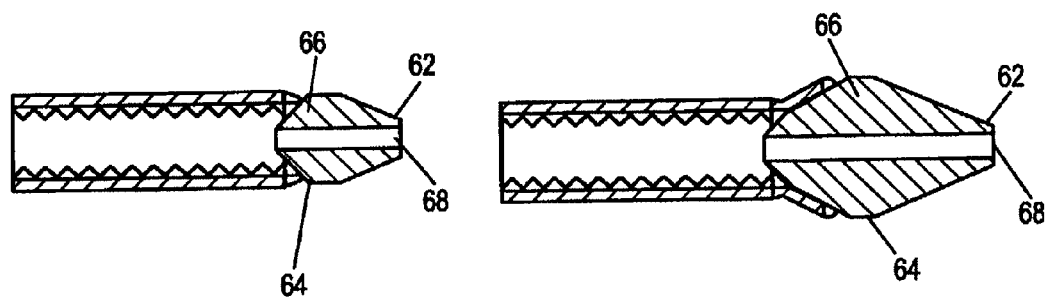
Fig. 6

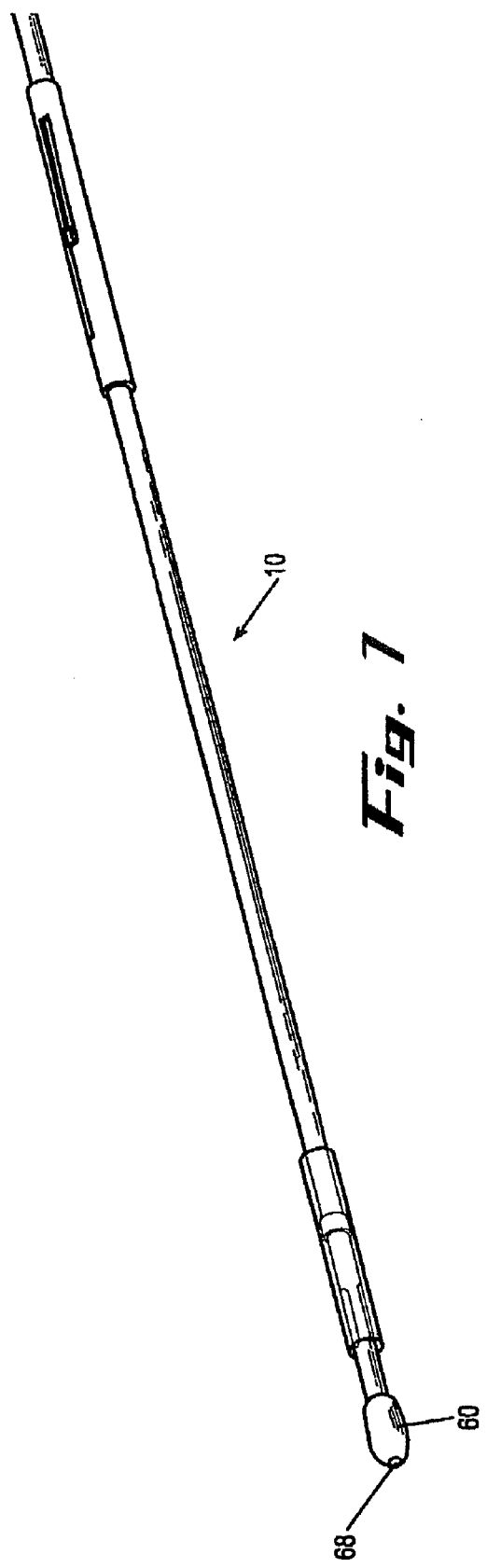
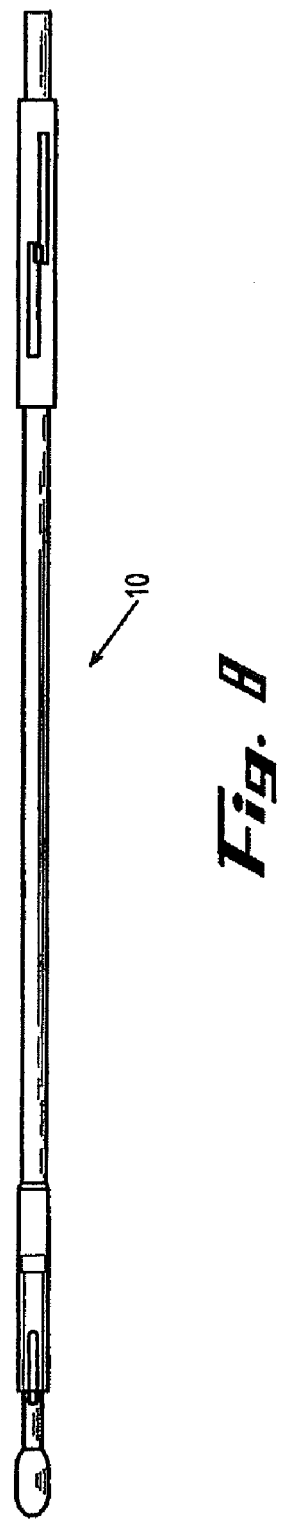

MEDICAL APPLIANCE OPTICAL DELIVERY AND DEPLOYMENT APPARATUS AND METHOD

FIELD OF THE INVENTION

The present invention relates generally to medical devices directed to the prevention of nonvascular vessel or passageway occlusion, and more particularly to stent deployment apparatuses and methods for utilizing these devices in the treatment of both benign and malignant conditions.

BACKGROUND OF THE INVENTION

Self-expanding stents are valuable prostheses for keeping lumen open and preventing closure due to a stricture, external compression, or internal obstruction. In particular, stents are commonly used to keep blood vessels open in the coronary arteries and they are frequently inserted into the ureters to maintain drainage from the kidneys, the bile duct for pancreatic cancer or cholangiocarcinoma or the esophagus for strictures or cancer. Additionally, stents may be formed specifically for alternative indications such as sealing a bleb, serving as a vehicle for drug administration or air removal from a bleb, etc.

Though stents are excellent devices when used properly, improper installation can lead to tissue luminal inflammation and tissue granulation. In particular, many physicians introduce stents with catheters and other delivery devices that do not give them adequate visual certainty that the device has been installed at the desired target site. Moreover, devices that allow for limited visual feedback have an excessively large diameter, which can hinder patient ventilation. Additionally, such devices do not have safety features to ensure that the stent is not prematurely and irretrievably deployed.

In order to facilitate the delivery of stents, medical device companies began to design deployment apparatuses that allow physicians to deploy stents more precisely. Unfortunately, guidance of the stent has substantially remained a function of physician skill resulting from substantial practice. This fact has become particularly evident with the advent of radially expanding stents. If after full deployment of the stent, the physician discovers the stent has been implanted incorrectly, there is no conventional way of correcting the error short of removing the stent. In particular, as a rule of thumb, once the exterior catheter, of conventional delivery devices, has been retracted beyond 60%, it generally cannot be realigned with respect to the stent. As a result, physicians must be sure of their stent placement prior to deploying the stent beyond the 60% point. We will refer to this 60% point throughout the application as the critical deployment point.

Conventional stent delivery devices, however, do not have any safety mechanism to prevent excessive deployment of a misaligned stent. In fact, conventional delivery devices require the physician to estimate extent of deployment, which results in either overly conservative or excessive deployment—both of which leads to stent misplacement.

Misplacement is often a function of a physician's inability to directly visualize the target area and the route thereto. Attempts have been made to provide scopes as postscript additions to existing devices, with little or no thought about the functionality of such arrangements. As a result visualization features are not directly integrated into the design of these devices and therefore substantially limit their efficacy.

An additional limitation of conventional stent delivery devices is the distal tip of conventional stent delivery devices are not adequately designed to (1) facilitate the clearance of obstructed lumen, or (2) facilitate the removal of the delivery device once the stent is radially expanded. In particular, most distal tips are not configured to comfortably guide the delivery device through a diseased or occluded lumen so that the stent can be delivered in the most beneficial location. Moreover, once the stent is radially expanded conventional designs rely exclusively on dimensional mismatching to ensure proper removal of the delivery device. In the event the stent does not adequately expand to preset dimensions, a conventional delivery device would be stuck in the patient until some invasive procedure is performed to remove it and the defective stent.

Therefore, there remains an existing need for a stent deployment apparatuses that has a safety mechanism to prevent excessive deployment of a misaligned stent. Preferably it would be desirable if the safety mechanism had a physical and/or audible indication means to inform the physician when she has reached maximum reversible deployment. As an additional safety feature, there is an existing need for a distal tip designed to allow for the removal of the deployment apparatus even if the stent does not radially expand to its preset expansion diameter. An existing need also exists for a stent deployment apparatus that has a distal tip adequately configured to navigate through diseased and/or occluded lumens so that the stent can be delivered to this target area.

There also remains an existing need for a stent deployment apparatus that increases physician control during stent deployment. Moreover, there exists a need for a stent deployment apparatus that allows for the insertion of an optical scope to facilitate stent delivery. In particular, there is an existing need for a delivery device that allows for the direct visualization of lumens via a variety of optical configurations. For example, optical scopes can be directly integrated into the inner dimensions of the device or receivable about the inner or outer dimensions of the inner and outer tubular members. Additionally, there is a need for a device that provides visualization windows to enhance the physician's field of view during deployment.

SUMMARY OF EXEMPLARY EMBODIMENTS

It is a principal objective of an exemplary stent deployment apparatus in accordance with the present invention to provide a device that can facilitate the precise delivery of stents in a safe and repeatable fashion. In the furtherance of this and other objectives, a preferred deployment apparatus allows the physician to concentrate on correct placement without having to estimate extent of deployment. In particular, in a preferred embodiment, the present deployment apparatus has a physical safety mechanism that limits deployment to the critical deployment point (i.e., ~60%). The critical deployment point may range from 5% to 95% but is preferably about 60%. At this point, if the physician is satisfied with placement, she can engage the safety means to what we refer to as the Proceed Orientation (PO) and fully deploy the stent. It is preferred that when the safety mechanism is engaged to the PO, a physical twist and a possible audible indicator sounds to inform the physician that if she deploys the stent any further, she can no longer retract the stent beyond this point. Though the present stent and delivery system eliminates the need for repositioning, such safety features are still preferable. In a preferred embodiment, the slight audible indication is the sound of a tab or stop snapping to allow free deployment of the stent.

An additional objective of a preferred embodiment of the present invention is to provide a stent deployment apparatus where the handle portion is held and the outer tubular member of the device is retracted.

Yet another objective in accordance with the present invention is to provide a deployment apparatus having a distal tip designed to facilitate the clearance of obstructed lumen. In the furtherance of this and other objectives, the exemplary distal tips are configured to comfortably guide the deployment apparatus through a diseased or occluded lumen so that the stent can be delivered in the most beneficial location.

Still another objective of a preferred deployment apparatus in accordance with the present invention is to provide a distal tip that facilitates the removal of the deployment apparatus once the stent is radially expanded. In the furtherance of this and other objectives, the distal tip is designed to clear the stent during removal, in the event the stent does not adequately expand to preset dimensions. In a preferred embodiment, removal is facilitated by providing a distal tip that has a substantially bidirectional conic shape. This allows for the removal of the present deployment apparatus, while conventional deployment apparatuses would be stuck in the patient until some invasive procedure was performed to remove it and the defective stent. This results from the fact that conventional deployment apparatus designs rely exclusively on dimensional mismatching between the distal tip and the radially expanded stent to ensure proper removal of the deployment apparatus. As a function of the design of the present invention, the compressed stent is adequately retained in place and does not prematurely creep up the proximally facing conic end of the distal tip and prematurely deploy.

An additional objective in accordance with an exemplary embodiment of the present invention is to provide a stent deployment apparatus that allows for the insertion of an optical scope to facilitate stent delivery. In the furtherance of this and other objectives, the device is capable of letting a flexible optical scope of about 5-6 mm diameter be coupled along the exterior of the outer tubular member thereof. Alternatively, it is envisioned that an ultra thin optical scope may pass along side the guidewire through the internal diameter of the inner tubular member of the device. In the furtherance of this and other objectives, the inner tubular member defines windows in the distal region to allow enhanced visualization of stent deployment. In accordance with this embodiment, the guidewire itself may be the scope.

An additional objective in accordance with an alternative embodiment of the present invention is to provide a stent deployment apparatus that has an outer tubular member of sufficient cross sectional thickness to define a plurality of longitudinally extending channels for receiving additional utility tools. In the furtherance of this and other objectives, and by way of example only, one such channel could accommodate an ultra thin scope while an alternative channel receives a guidewire, syringe systems, etc. Principally, these channels are suitable for receiving a number of other tools that a physician may need during deployment of a stent or therapeutic treatment of target tissue.

Still another objective in accordance with a preferred embodiment of the present invention is to provide a device having direct visualization capabilities directly incorporated into the device. In one design of such embodiment, the inner tubular member in general and the distal tip in particular serve as an optical device. Moreover, in embodiments where the outer tubular member and distal tip have utility channels and/or grooves, the channels and grooves may themselves be comprised in whole or in part by optically active materials. In the furtherance of this and other objectives, the internal tubular member comprises at least one optical fiber coupled to a lens and light source to provide direct visualization during deployment. Though the above specified safety mechanism is not necessary with direct visualization, the safety mechanism may accompany this embodiment.

In addition to the above objectives, an exemplary stent deployment apparatus preferably has one or more of the following characteristics: (1) applicable for tracheal respiratory bronchial stenosis; (2) biocompatible; (3) compliant with radially expanding stents; (4) capable of distal or proximal stent release; (5) smooth and clean outer surface; (6) length of the device variable according to the insertion procedure to be employed; (7) outer dimension as small as possible (depends on the diameter of crimped stent); (8) dimensions of the device must offer enough space for the crimped stent; (9) radiopaque markers, preferably on the inner tubular member, to indicate proximal and distal ends of the stent; (10) sufficient flexibility to adapt to luminal curvatures without loss of ability to push or pull; (11) low friction between the inner tubular member and outer tubular member; (12) sufficient resistance to kinking; (13) good deployment; ability to reposition partially deployed stent; (14) added with a scale to observe the stent position during the insertion procedure; (15) insertion procedure should require low force; or (16) sufficiently economical to manufacture so as to make the deployment apparatus disposable.

Further objectives, features and advantages of the invention will be apparent from the following detailed description taken in conjunction with the accompanying drawings.

BRIEF DESCRIPTION OF THE FIGURES

FIG. 5 is an enlarged sectional view of a distal tip with direct visualization capabilities, in accordance with the present invention, showing the lens, light source and working channel portions thereof;

FIG. 6 depicts cross sectional views of various distal tips in accordance with the present invention;

FIG. 7 is a perspective view of an alternative device for delivering and deploying a radially self-expanding stent in accordance with the present invention;

FIG. 8 is a side view of the device for delivering and deploying a radially self-expanding stent in accordance with the present invention.

DETAILED DESCRIPTION OF AN EMBODIMENT

Figure 1:
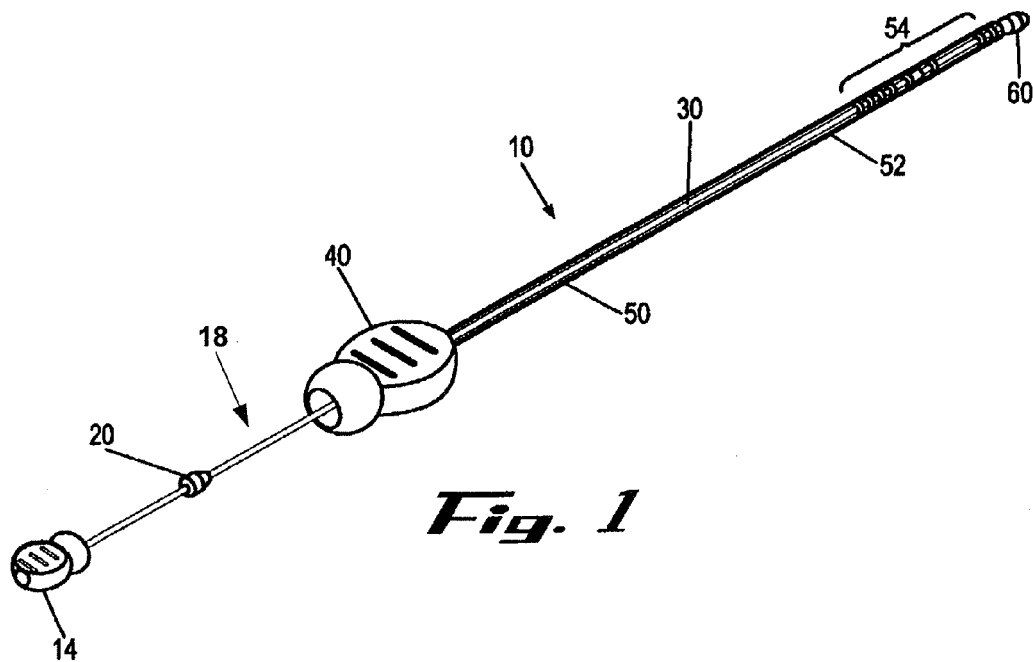
FIG. 1 is a perspective view of a device for delivering and deploying a radially self-expanding stent in accordance with the present invention.

A general problem in the diagnosis and therapy of pulmonary defects, bronchial defects, tracheal defects and many other nonvascular anomalies is the fact that the instruments must be inserted from the mouth or the nose into the larynx or the trachea, wherein it is necessary to pass the area of maximum diameter of about 15 mm. As a result, the inserted instruments take away a very large portion of the free lumen. Consequently, in respiratory lumens spontaneous respiration of the patient is impaired. In addition, there is the danger of injuring the patient.

Therefore, it is a principal objective of the present invention to provide an instrument, which can be inserted gently, ensures a good utilization of the available space and makes it possible to carry out active therapeutic measures, wherein the instrument is to be particularly suitable for the introduction and placement of stents. It is also within the scope of the present invention to provide a device adaptable for placement in a variety of target sites in a patient's anatomy. In other words, devices in accordance with the present invention should in no way be limited to pulmonary delivery devices as such devices are suitable for a broader range of indications.

A preferred embodiment of the present deployment apparatus comprises inner and outer tubular members interactively coupled with each other in a manner that one can move rotationally and proximally or distally with respect to the other. The tubular members are preferably nonpyrogenic. In order to deliver the stent, the deployment apparatus comprises a distal tip and a stent-retaining hub, between which the stent is placed. The distal tip and the stent-retaining hub are both functionally coupled with the inner tubular member. The inner tubular member terminates with the proximal handpiece. The proximal handpiece is preferably a female threaded proximal handpiece, but alternative termini are within the skill of the stent deployment device engineer. In fact, a suitable alternative would be a handle having similar internal diameter characteristics as the proximal handpiece while providing greater surface area for manipulating the deployment apparatus. The deployment apparatus is preferably sterilized by a validated sterilization cycle EtO. Moreover, the device is capable of resterilization (validated cycle) with no degradation of performance. However, it is preferable to provide a disposable device.

The total length of the deployment apparatus varies based on the location of the target lumen. For purposes of this discussion, the usable length of the inner tubular member shall be from the inner tubular member distal hub/handle end to the distal tip. The usable length of the outer tubular member shall be from the distal hub/handle end of the outer tubular member to the distal tip. The overall length of the device shall be from the distal hub/handle end of the outer tubular member to the distal tip of the inner tubular member when assembled and not deployed. There are preferably three radiopaque (platinum iridium) markers for marking the stent, the stent deployment distance, and depth. The outer tubular member is preferably manufactured of stiffer synthetic material. In a preferred embodiment, the length of the outer tubular member is preferably shorter than that of the inner tubular member.

However, these dimensions may differ as a function of the stent diameter and/or if an optical scope is integrally provided to facilitate stent delivery. The outer tubular member may be configured to allow for the coupling of an optical stent along the exterior diameter thereof. Alternatively, the interior diameter of the inner tubular member may be enlarged sufficiently to accommodate the optical scope and additionally the increased crimped stent diameter. However, it is expected, though not required, that the smallest diameter that allows for example a bronchoscope to pass will be employed in this alternative embodiment. It should be understood that through hindsight, after exposure to the present specification, one of ordinary skill would be able to adapt the current device to receive an ultra thin optical scope to the internal diameter of the device without undo experimentation and without departing from the spirit of the present objectives.

In an alternative embodiment, an integrated direct visualization system is provided wherein an optical cable is coupled with a portion of or comprises the hypotube and preferably capable of extending beyond both the distal and proximal ends of the deployment device such that viewing of any segment of the lumen is possible. In such embodiments, the camera and light source are preferably operatively coupled and disposed about the distal region of the apparatus.

An exemplary deployment apparatus in accordance with the present invention is durable while affording adequate flexibility to navigate through anatomical lumens without kinking. To this end, it is preferable that the deployment apparatus is formed of biocompatible synthetics and in a preferred embodiment reinforced with metal structure. This allows for deployment within an accuracy of about ±3 mm. Moreover, the stent is preferably released with a force lower than 30 Newtons at 37° C.

The inner tubular member is composed of a thin elastic synthetic material, such as polyurethane or Teflon®. At its proximal end, the inner tubular member has a standard adaptor or connector. At its distal end, the inner tubular member is equipped with a tip specific for various anatomical lumens.

The inner tubular member and the outer tubular member can be displaced relative to each other in longitudinal direction as well as in a radial direction. The deployment apparatus in accordance with the present invention can be used most advantageously for the placement of stents. Such stents are available in various embodiments of metal and/or synthetic material. They usually are composed of a fabric of metal wires, which expand by themselves as a result of their natural tension. Stents of a so-called shape memory alloy are also known. These stents have a small radial diameter at a low temperature, while they expand radially when exceeding an upper threshold temperature, so that they can keep a stenosis open in this manner. It is particularly advantageous to use stents of an alloy of nickel and titanium, the so-called nitinol.

An exemplary deployment apparatus according to the present invention can be used for the placement of various stents, whether they are self-expanding stents or stents, which require activation. For this purpose, the stent is placed in the free space between the outer tubular member and the inner tubular member. Positioning of the stent in the deployment apparatus can be carried out in the area between the tip and the stent-retaining hub at the distal end of the inner tubular member. Alternatively, in its insertion position, fasteners or other suitable retaining elements may hold the stent.

In relevant embodiments, when the stent is inserted and after the stenosis has been passed, the outer tubular member is retracted, so that the stent is released. Alternatively, the distal end of the outer tubular member may be placed about the stenosis so that the inner tubular member may be extended so that the stent is placed in direct contact with the desired location prior to expansion. A self-expanding stent then by itself assumes the expanded position. This eliminates the need for post expansion positioning techniques. With an alternative embodiment of the device, the device has fasteners that retain contact with a portion of the stent in the event that the stent needs to be retracted or repositioned. A stent suitable for such procedures would be one in accordance with the disclosure in co-pending U.S. patent application Ser. No. 10/190,770, which is incorporated herein in its entirety by this reference.

The following reference numbers and corresponding stent placement and deployment device components are used when describing the device in relation to the figures:

10 Stent Delivery & Deployment Device
12 Guidewire
14 Proximal Handpiece
16 Hypotube
18 Safety Mechanism
20 Stop
22 Female Locking Member on the Stop
24 Tab of the Stop
30 Inner Tubular Member
32 Interior Diameter of Inner Tubular Member (Working Channel)
34 Exterior Diameter of Inner Tubular Member
40 Handle
42 Cavity in Proximal Portion of Handle
43 Inner Channel of Handle
44 Base of Handle Cavity
46 Male Locking Member
48 Inner Handle Hub
49 Outer Handle Hub
50 Outer Tubular Member
52 Exterior Diameter of Outer Tubular Member
54 Distal Region of Outer Tubular Member
55 Utility Channels of Outer Tubular Member
56 Interior Diameter of Outer Tubular Member
58 Exterior Tubular Member Utility Channel
60 Distal Tip
62 First End of the Tip
64 Medial Region of the Tip
66 Second End of the Tip
68 Axial Passage
70 Retaining Hub
72 Distal Region of Retaining Hub
74 Proximal Hub of Retaining Hub
76 Pusher
80 Proximal Marker
82 Medial Marker
84 Distal Marker
90 Detent on Hypotube
100 Stent
110 Beveled Optical Window
118 Channel Safety Mechanism
120 Optical Instrument
122 Optical Instrument Proximal Region
124 Optical Instrument Distal Region
126 Optical Instrument Light Source Connection
128 Optical Instrument Lens Connector
130 Guidewire Receiving Member
140 Outer Tube
142 Safety Track
144 Safety Catch
150 Utility Grooves of Distal Tip
152 Utility Channels of Distal Tip
160 Light Source
170 Lens
180 Camera It should also be pointed out at the outset that various embodiments of stent delivery and deployment devices in accordance with the present invention make reference to guidewires and/or optical instruments. In some embodiments the terms may overlap since it is contemplated within the scope of such embodiments that the guidewire itself has visualization capabilities resulting from the guidewire being an ultra thin optical and/or ultrasound device. It should also be evident from the following disclosure that independent placement of traditional and visualization capable guidewires as well as guidewires integrally coupled with the device for placement and deployment of a stent is contemplated and should be considered as residing within the scope of the claims.

Figure 2:
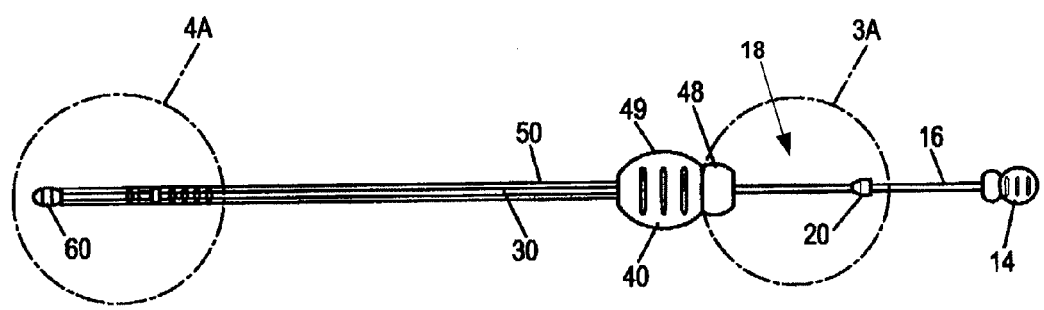
FIG. 2 is a side view of the device for delivering and deploying a radially self-expanding stent in accordance with the present invention.
Figure 3A:
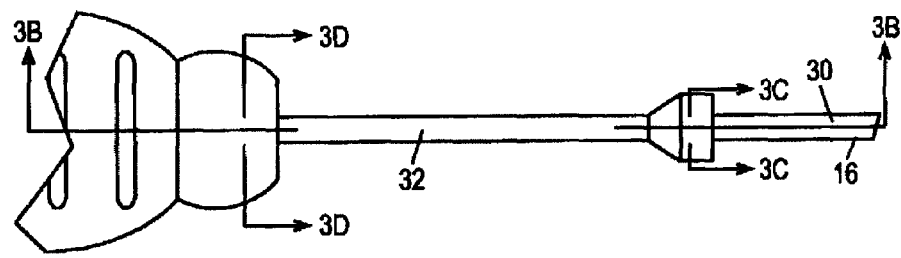
FIG. 3A depicts enlarged views of portions of the deployment safety mechanism along lines 3A-3A of the device of FIG. 2
Figure 3B:
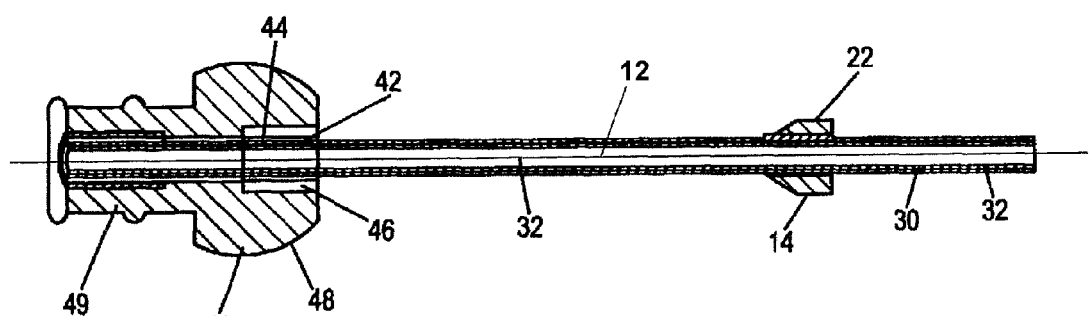
FIG. 3B shows a cross section view of the deployment safety mechanism along lines 3B-3B of FIG. 3A.
Figures 3C, 3D:
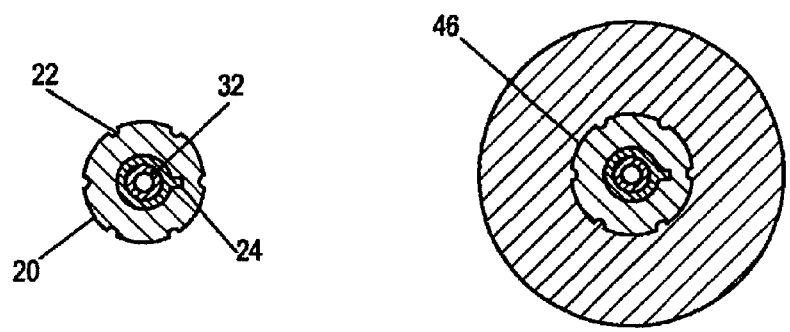
FIG. 3C is a perspective view of a portion of the complementary portion of the deployment safety mechanism region of the handle as shown along lines 3C-3C of FIG. 3A.
FIG. 3D is a perspective view of the stop of the deployment safety mechanism as shown along lines 3C-3C of the device of FIG. 3A.

The figures show an exemplary placement and deployment device 10 in accordance with the present invention. Referring in particular to FIGS. 1-2, the present invention provides a stent deployment apparatus 10 that includes an outer tubular member 50 and an inner tubular member 30, wherein the outer tubular member 50 and the inner tubular member 30 can be displaced relative to each other. At the proximal end of an exemplary device 10 is a proximal handpiece 14, coupled with a portion of the inner tubular member 30 and preferably a portion of a hypotube 16. Note that the hypotube throughout this specification may refer to a standard catheter hypotube or alternatively a single or bundle of optical fiber for use in the direct visualization embodiments in accordance with the present invention. As stated earlier, a suitable alternative terminus may be employed as long as it provides the minimum benefits provided by a proximal handpiece. The hypotube 16 is disposed about the inner tube 30 and extends from a location adjacent to the proximal handpiece 14 through a portion of the handle 40 of the deployment apparatus 10. In an alternative embodiment, the hypotube 16 terminates within the proximal handpiece 14. A safety mechanism 18 is provided that is formed in part by the complementary fitting of a portion of the handle 40 and a stop 20 coupled with the hypotube 16 between the proximal handpiece 14 and the handle 40. The stop 20 is preferably molded onto the hypotube 16, the molding process resulting in a tab 24 formed on the stop 20 that is subsequently broken when the physician desires to place the deployment apparatus 10 in the proceed orientation. In an exemplary embodiment, when the tab 24 is broken and the deployment apparatus 10 is placed in the proceed orientation; the stop 20 may potentially rotate freely about the hypotube 16.

As illustrated in FIGS. 3A-3D, a preferred stop 20 includes female locking members 22 comprising channels formed along the exterior thereof that are complementary to the male locking members 46 formed on the interior cavity 42 along the proximal region of the handle 40. The male locking members 42 and female locking members 22 can be formed into any shape or suitable size as long as they do not depart from the essential purpose of forming a safety mechanism. The cavity 42 of the handle 40 is designed to receive the stop 20 and prevent further deployment. As a result, the stop 20 is molded at a distance along the hypotube 16 such that the distance between the distal end of the stop 20 and the base 44 of the complementary cavity 42 of the handle 40 roughly corresponds to the critical deployment point. It should be noted that the female locking members 22 and male locking members 46 of the safety mechanism 18 might be reversed so that the female locking members 22 and male locking members 46 are on the handle 40 and the stop 20, respectively. Additionally, alternative safety mechanisms, varying in size, shape and manner, may be employed to ensure accurate deployment beyond the critical deployment point.

The handle 40 is preferably molded to a portion of the outer tubular member 50, which extends from the handle 40 to the distal tip 60 of the device 10. The outer tubular member 50 is disposed about the inner tubular member 30. In an exemplary embodiment, the outer tubular member 50 is clear so that the inner tubular member 50 is visible there through. Moreover, markers 80-84 preferably formed on portions of the inner tubular member 30 are also visible through the outer tubular member 50.

Figure 4A:
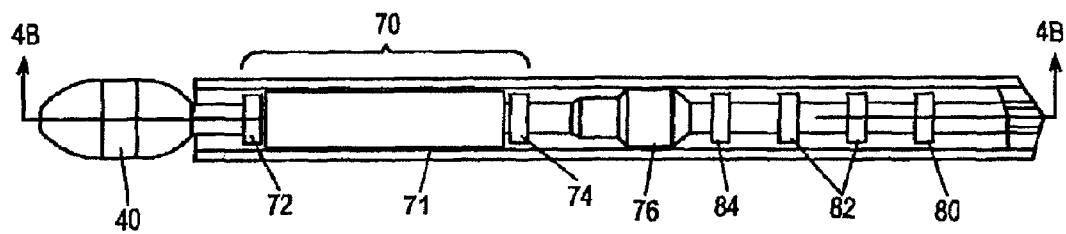
FIG. 4A is a side perspective view of the distal region of the device of FIG. 2, along lines 4A-4A.
Figure 4B:
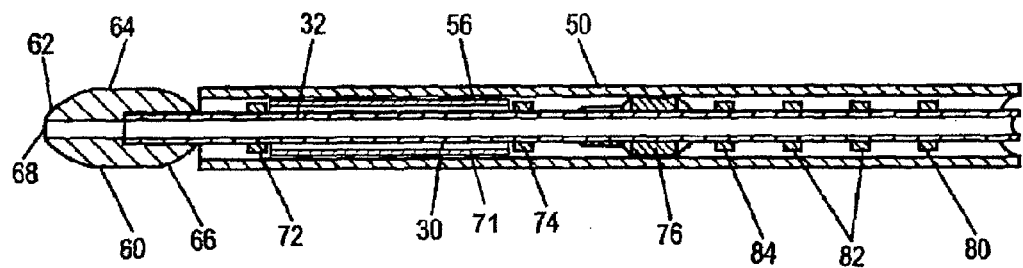
FIG. 4B depict an enlarged sectional view of the distal region of the device of FIG. 2, along lines 4B-4B.
Figure 4C:
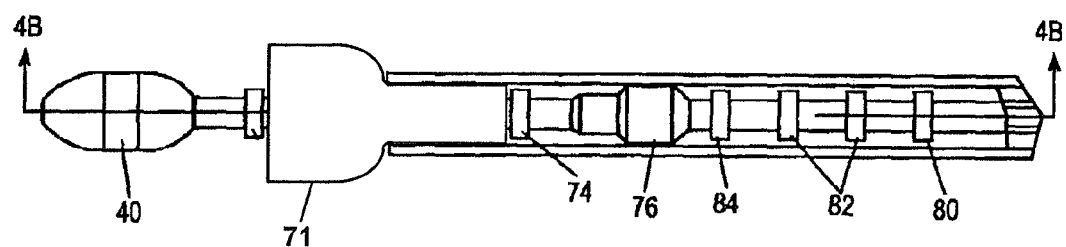
FIG. 4C depicts an enlarged sectional view of the distal region of the device of FIG. 2, with the stent partially deployed at a critical deployment point.
Figure 9:
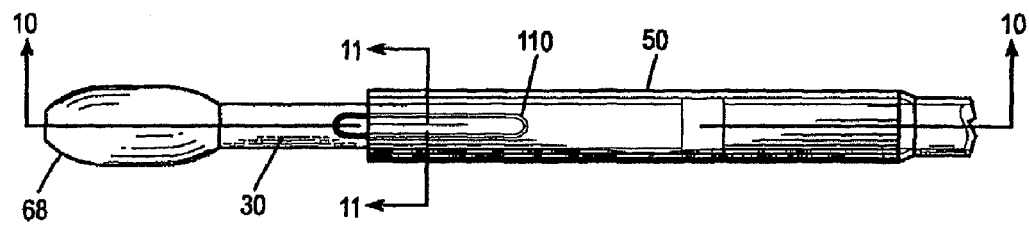
FIG. 9 is a side view of the distal region of a device for delivering and deploying a radially self-expanding stent in accordance with the present invention.
Figure 10:
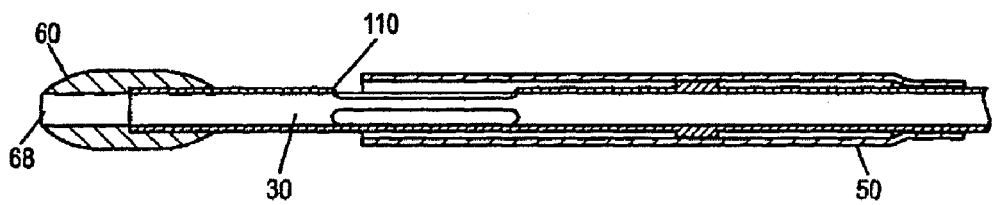
FIG. 10 depicts an enlarged cross sectional view of portions of the deployment visualization features along lines 10-10 of the device of FIG. 9.

Referring now to FIGS. 4A-4C, in the distal region 54 of the device 10, there is a stent-retaining hub 70, which holds the stent 71 during the placement procedure. In a preferred embodiment, the stent-retaining hub 70 comprises two double conical shaped elements, one disposed at each end of the stent 71 and coupled with the inner tubular member 30. In an exemplary form, the distal most double conical shaped element is the distal tip of the device 60. In alternative embodiments, the stent-retaining hub 70 may also comprise proximal 72 and distal 74 stops between which the stent 71 rests in its crimped state. The stent-retaining hub 70 may be removable so as to allow a pre-sterilized, crimped stent containing, hub 70 to be installed in the distal region of the device for stent delivery and deployment. Moreover, the proximal end of the stent 71 may also be restrained by conventional coupling methods (not shown) to facilitate retrieval if necessary. By way of example, which is in no way to be construed as limiting, a stent having suture disposed about its proximal end may be retained by the stent-retaining hub 70 that has releasable finger-like members engaging the suture.

The device is configured such that an optional guidewire 12 may be passed through the internal diameter 32 of the device through the proximal handpiece 14 at the proximal end, the distal tip 60 at the distal end and the inner tubular member 30 there between. In an alternative embodiment, the internal diameter 32 of the device 10 is sufficient to receive an optical scope there through. In this alternative embodiment, the optical scope may pass about the guidewire 12 from the proximal to and through the distal ends of the deployment apparatus 10. This is so as to allow the physician to view a patient's anatomy that may lie distal of the distal tip 60 of the deployment apparatus 10. In an additional embodiment, a single fiberscope may be provided that is coupled with the guidewire.

Additionally, the outer tubular member 50 and the inner tubular member 30 may be adapted so that instead of feeding the optical scope through the proximal handpiece 14, the mating apertures are formed along a portion of the longitudinal expanse of the inner tubular member 30 and an entry point formed on a portion of the outer tubular member so as to receive the scope through both the inner tubular member 30 and the outer tubular member 50 even as the inner tubular member 30 and outer tubular member 50 are moved rotationally and proximally or distally with respect to the other.

Figure 17:
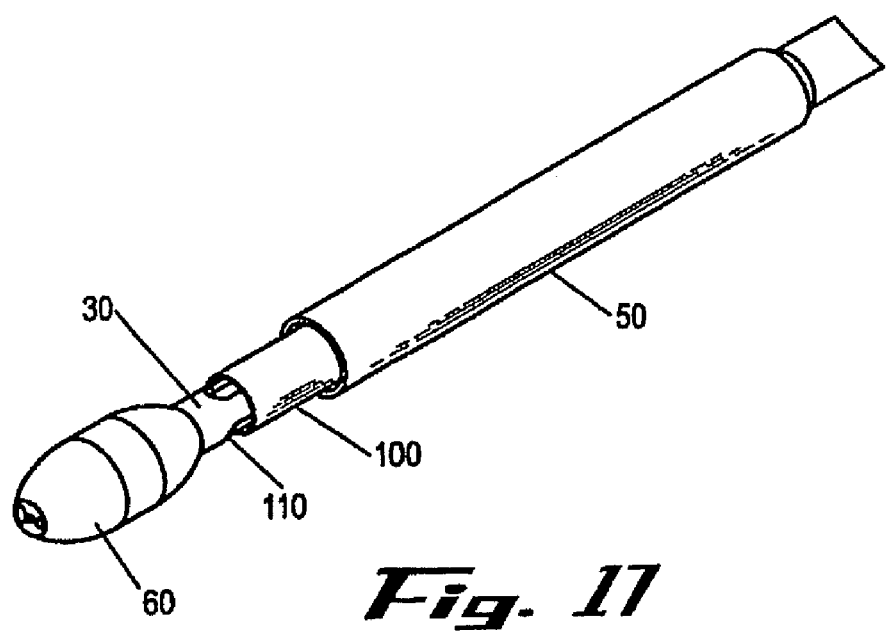
FIG. 17 is a sectional view of the deployment apparatus shown in FIG. 15.

As an alternative, shown specifically in FIGS. 5 & 17, a deployment device is provided that has a distal tip 60 having a light source 160, lens 170 and working channel 32 operatively configured therein to allow direct visualization of the target site.

Figure 18:
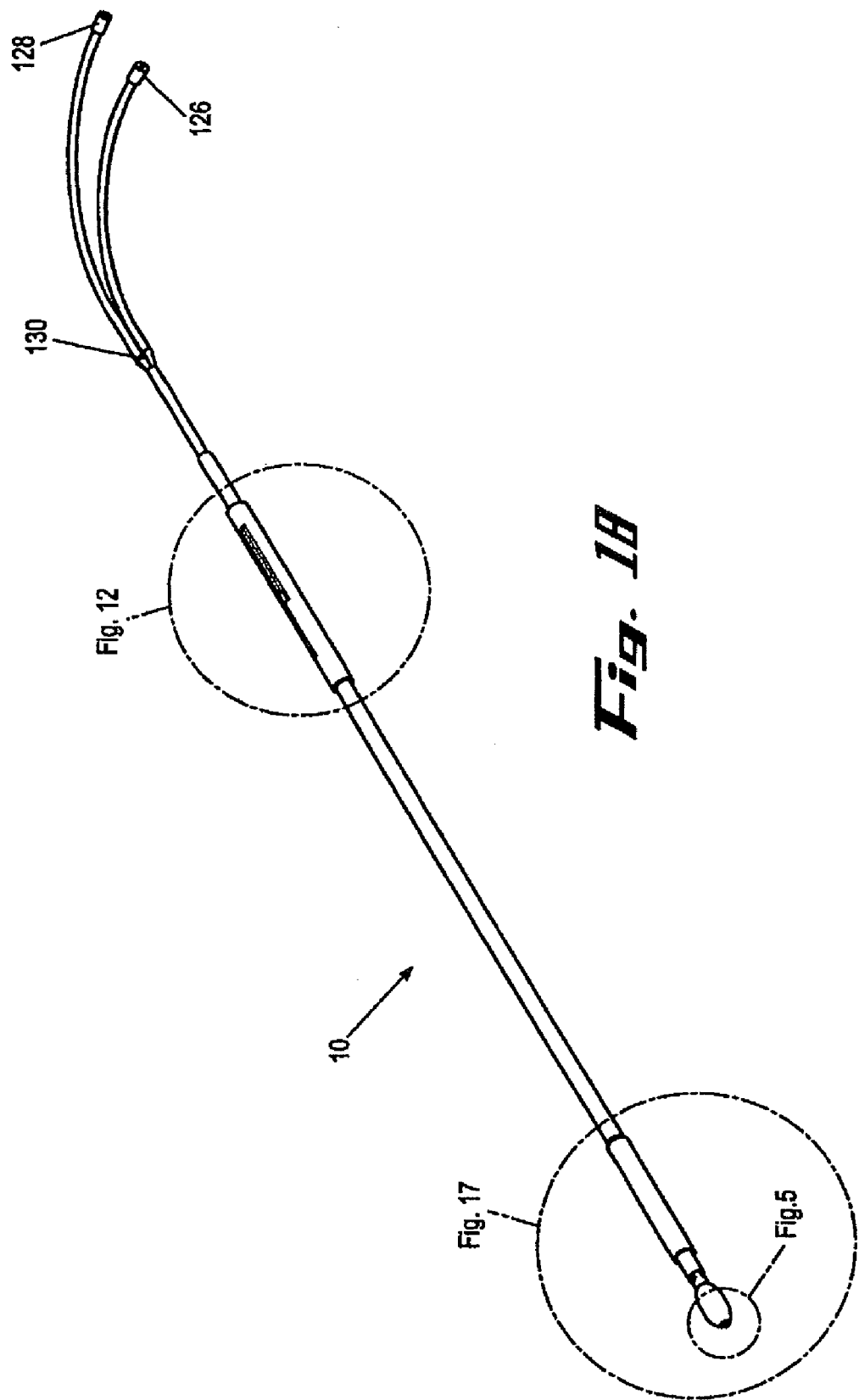
FIG. 18 is a perspective view of a deployment apparatus, as shown in FIG. 15, further comprising a parallel channel for receiving and extending a guidewire.
Figure 19:
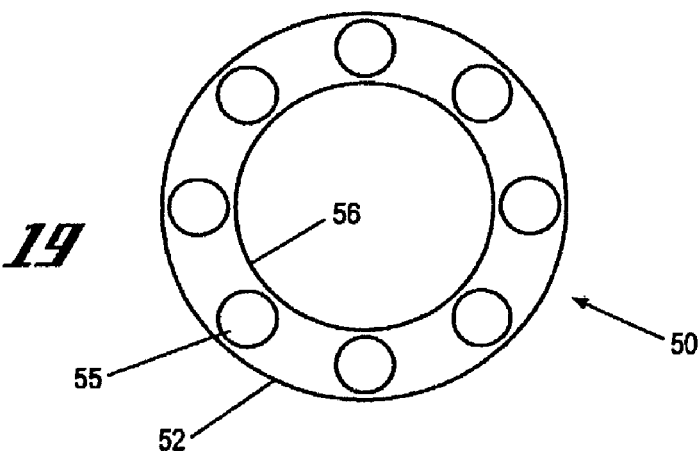
FIG. 19 is a cross sectional view of an outer tubular member in accordance with a preferred embodiment of the present invention wherein the outer tubular member defines a plurality of longitudinally extending apertures between the inner and outer surfaces thereof forming utility channels.

The present invention, in alternative embodiments shown in FIGS. 18-19, provides deployment devices wherein guidewires 12; optical instruments 120 and other therapeutic tools may be provided through alternative means. Referring in particular to FIG. 18, about the proximal handle 14, a guidewire receiving member (not shown) and an optical instrument receiving member (not shown) are provided that allows one or both of these devices to travel to the distal tip 60 of the device 10 via the internal diameter 32 of the inner tubular member 30. Preferably, an optical instrument 120 is coupled with a portion of inner tubular member 30 and extends beyond both the distal and proximal ends thereof. The optical instrument 120 may be configured to have an external light source that is connected by the light source connector 126. Moreover, a CCD or Lens is connected to the optical instrument 120 by connector 128. In this preferred embodiment, the optical device allows for the visual display on conventional display means known in the art. The device 10 may also be configured so that the guidewire 12 and/or the optical instrument 120 can pass between the light source connector 126 and the lens connector 128, obtaining access to either the inner tubular member 30 or the outer tubular member 50.

Yet another and preferred embodiment of a deployment device in accordance with the present invention is the device 10 as shown in FIG. 19, wherein the outer tubular member 50 defines a plurality of longitudinally extending utility channels 55 between the inner 56 and outer surfaces 52 of the outer tubular member 50. In this embodiment, an optical instrument 120, guidewire 12, or other medical appliance may be disposed through these channels to provide therapeutic results. In a preferred embodiment the channels extend longitudinally from the proximal to the distal ends of the outer tubular member 50 and may also themselves define openings (not shown) that allow the preferred medical appliance (e.g., optical instrument, guidewire, etc) to enter the inner tubular member at locations between the distal and proximal ends thereof. To this end, in this particular embodiment, the openings may be formed through both the inner surface 56 of the outer tubular member 50 and potentially both the inner 32 and outer 34 surfaces of the inner tubular member 30.

Figure 15:
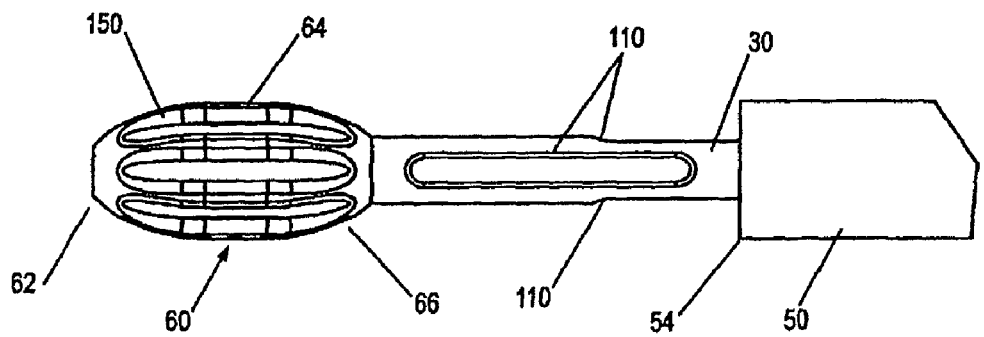
FIG. 15 is a perspective view of a portion of a device for delivering and deploying a radially self-expanding stent having optical windows that are staggered in orientation and wherein the distal tip has channels formed on the outer surface thereof to facilitate the ingress and egress of utility tools passed through the outer tubular member.
Figure 16:
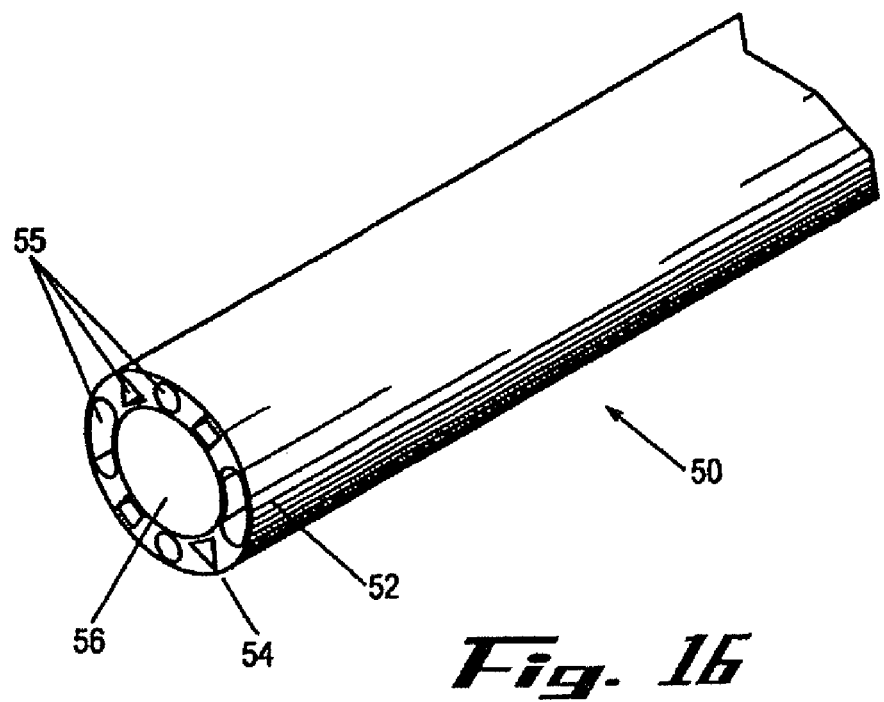
FIG. 16 is a perspective view of a preferred embodiment of a deployment apparatus showing a variety of optional geometries of the working channels formed between the interior and exterior diameters of the outer tubular member.

As an extension of FIG. 19, FIGS. 15-16 & 22 show a deployment device 10 that has an outer tubular member 50 having a plurality of utility channels 55 for passing instruments and devices, useful during a procedure, through the device 10 to the target location. As shown in FIG. 15, distal tip 60 has complementary utility grooves 150 to allow the instruments and devices to pass beyond the distal end of the outer tubular member 50. FIG. 15 also shows the advantage of having optical windows 110 in general and staggered optical windows 110 in particular to optimize visualization proximal the distal tip 60. An example of a suitable instrument passed along the utility channels 55 of the outer tubular member 50 and the utility groove 150 of the distal tip 60 would be a guidewire 12, though many other useful instruments may be employed, limited only by the need to keep the exterior diameter 52 of the outer tubular member 50 within a range that can fit in the lumen in which the device 10 will be introduced. Moreover, the guidewire could be a standard guidewire, or alternatively a specialized ultra thin guidewire having optical capabilities.

An alternative instrument is a syringe system (not shown) that can be integrally coupled with the delivery and deployment device 10 or alternatively configured to pass through either the working channel 32 or 56 of the inner 30 or outer 50 tubular members, respectively, or the utility channels 55 of the outer tubular member 50. An exemplary syringe system may have thermotherapy, cryotherapy, photodynamic, chemotherapy capabilities or combinations of these capabilities. In either configuration, but particularly the chemotherapeutic embodiment, the syringe system provides an extendable/retractable needle for delivering a therapeutic dose of a bioactive product such as a chemotherapeutic agent. It should be noted that the needle may alternatively be, for example, an electrocautery probe, for certain thermotherapy indications, or the bioactive product may be a suitable photosensitizer, in certain photodynamic therapy indications. Therefore, in order to adapt to the desired capabilities and a variety of indications, the general syringe system may be adapted in accordance with methods known in the art without requiring undue experimentation. It is preferable, in the chemotherapeutic and/or the photodynamic application, however, that the needle be introduced into a target lesion and the bioactive product introduced. It should be noted that the syringe system is useful in both malignant and benign applications. In a preferred embodiment, the syringe system comprises a needle at the distal end and a reservoir of bioactive product proximally situated, with a conduit servicing the needle and reservoir there between. The syringe system is configured to provide for extension and/or retraction of the needle to a target site in both the stand alone and integrated configurations. The stand-alone version is a general reference to the embodiment that is suitable for situating through appropriate channels of the device, but is not coupled thereto.

The various utility instruments referenced above, may take the form of a number of devices but, by way of non-limiting example, an exemplary photodynamic therapy device would have essential features of U.S. Pat. No. 6,454789B1 to Chen et al., which is incorporated in its entirety by this reference; an exemplary thermotherapy device would have essential features of U.S. Pat. No. 6,488,697 to Ariura et al., which is incorporated in its entirety by this reference; an exemplary cryotherapy device would have essential features of U.S. Pat. No. 6,514,245B1 to Williams et al., which is incorporated in its entirety by this reference; and an exemplary electrocautery device would have essential features of U.S. Pat. No. 6,156,035 to Songer, which is incorporated in its entirety by this reference. The syringe system may alternatively be configured for sealing a bleb, serving as a vehicle for drug administration or air removal from a bleb, etc. Therefore, it would be within the capacity of one of ordinary skill in the relevant medical device art to adapt such utility instruments for use with or as an integrated component of the present invention without undue experimentation.

With respect to the bioactive product, it may be a variety of therapeutic substances, but for chemotherapeutic indications, it may comprise a wide variety of chemotherapeutic agents such as but not limited to the exemplary chemotherapeutic agents like cis-platinum, paclitaxol, 5-flourouracial, gemcytobine and navelbine. The chemotherapeutic agents are generally grouped as DNA-interactive Agents, Antimetabolites, Tubulin-Interactive Agents, Hormonal agents and others such as Asparaginase or Hydroxyurea. Each of the groups of chemotherapeutic agents can be further divided by type of activity or compound. The chemotherapeutic agents used in combination with the anti-cancer agents or benzimidazoles of this invention include members of all of these groups. For a detailed discussion of the chemotherapeutic agents and their method of administration, see Dorr, et al, *Cancer Chemotherapy Handbook*, 2d edition, pages 15-34, Appleton & Lange (Connecticut, 1994) herein incorporated by this reference.

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercaldting topoisomerase II inhibitors such as, Etoposide and Teniposide; and the DNA minor groove binder Plicamycin. The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, or sulfhydryl group in nucleic acids, proteins, amino acids, or glutathione. The mechanism and the role of these alkylating agents in cancer therapy are not well understood. Typical alkylating agents include: Nitrogen mustards, such as Chlorambucil, Cyclophosphamide, Isofamide, Mechlorethamine, Melphalan, Uracil mustard; aziridines such as Thiotepa; methanesulfonate esters such as Busulfan; nitroso ureas, such as Cannustine, Lomustine, Streptozocin; platinum complexes, such as Cisplatin, Carboplatin; bioreductive alkylator, such as Mitomycin, and Procarbazine, Dacarbazine and Altretamine; DNA strand breaking agents include Bleomycin; DNA topoisomerase II inhibitors include the following: Intercalators, such as Amsacrine, Dactinomycin, Daunorubicin, Doxorubicin, Idarubicin, and Mitoxantrone; nonintercalators, such as Etoposide and Teniposide. The DNA minor groove binder is Plicamycin.

The Antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The Antimetabolites useful herein include: folate antagonists such as Methotrexate and trimetrexate pyrimidine antagonists, such as Fluorouracil, Fluorodeoxyuridine, CB3717, Azacytidine, Cytarabine, and Floxuridine purine antagonists include Mercaptopurine, 6-Thioguanine, Fludarabine, Pentostatin; sugar modified analogs include Cyctrabine, Fludarabine; ribonucleotide reductase inhibitors include Hydroxyurea.

Tubulin Interactive agents act by binding to specific sites on Tubulin, a protein that polymerizes to form cellular microtubules. Microtubules are critical cell structure units. When the interactive agents bind on the protein, the cell cannot form microtubules Tubulin Interactive agents include Vincristine and Vinblastine, both alkaloids and Paclitaxel.

Hormonal agents are also useful in the treatment of cancers and tumors. They are used in hormonally susceptible tumors and are usually derived from natural sources. These include: estrogens, conjugated estrogens and Ethinyl Estradiol and Diethylstilbestrol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone; Adrenal corticosteroids are derived from natural adrenal cortisol or hydrocortisone. They are used because of their anti-inflammatory benefits as well as the ability of some to inhibit mitotic divisions and to halt DNA synthesis. These compounds include Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include antiestrogenic agents such as Tamosifen, antiandrogen agents such as Flutamide; and antiadrenal agents such as Mitotane and Aminoglutethimide. Hydroxyurea appears to act primarily through inhibition of the enzyme ribonucleotide reductase. Asparaginase is an enzyme that converts asparagine to nonfunctional aspartic acid and thus blocks protein, synthesis in the tumor. It should also be noted that the bioactive product may include as much as about 99.9% chemotherapeutic agent to as little as <1% chemotherapeutic agent or any amount there between.

Figure 22:
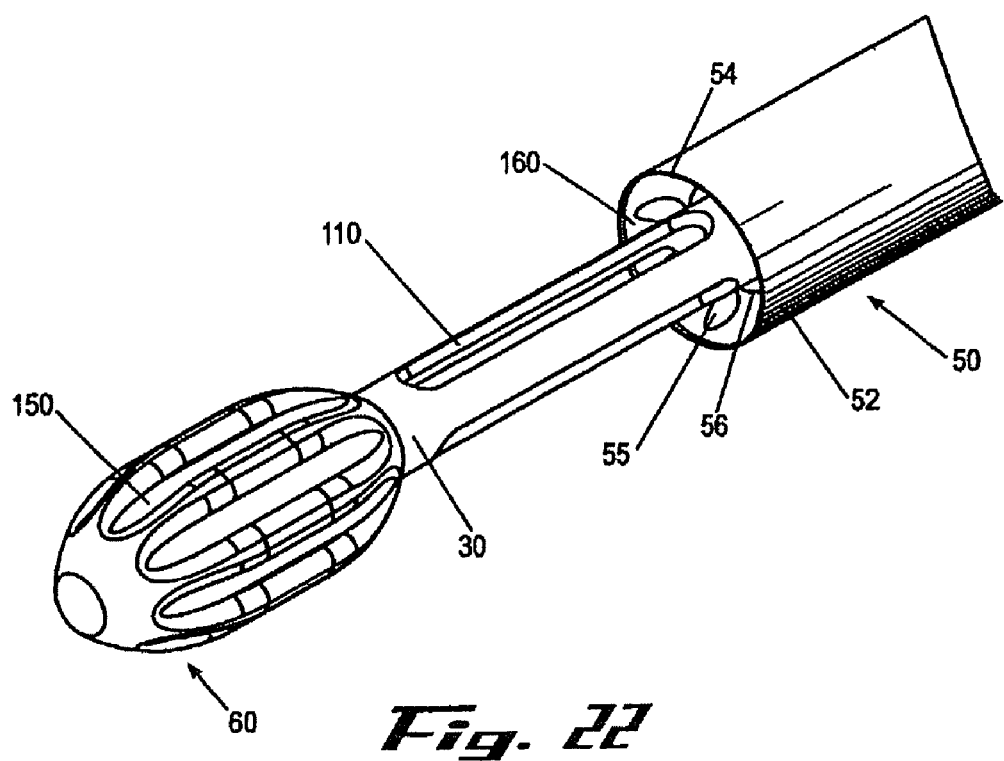
FIG. 22 is a perspective view of a preferred embodiment of a delivery and deployment device in accordance with the present invention, wherein the distal tip has utility grooves and the outer tubular member has a substantially beveled distal region for receiving the proximal end of the distal tip.

Also, as shown in FIG. 22, the distal region 54 of outer tubular member 50 may be beveled to allow a portion 66 of distal tip 60 to be covered by a portion of outer tubular member 50 without obstructing either the utility channels 55 of the outer tubular member 50 or the utility grooves 150 on the distal tip 60. Alternatively, the distal tip 60 may be beveled to receive the distal most portion of the outer tubular member 50.

Figure 20:
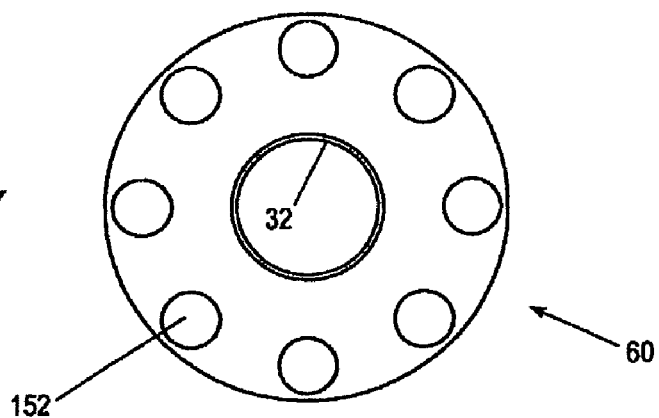
FIG. 20 is a frontal view of the distal tip showing apertures complementary to the utility channels shown in FIG. 19.
Figure 21:
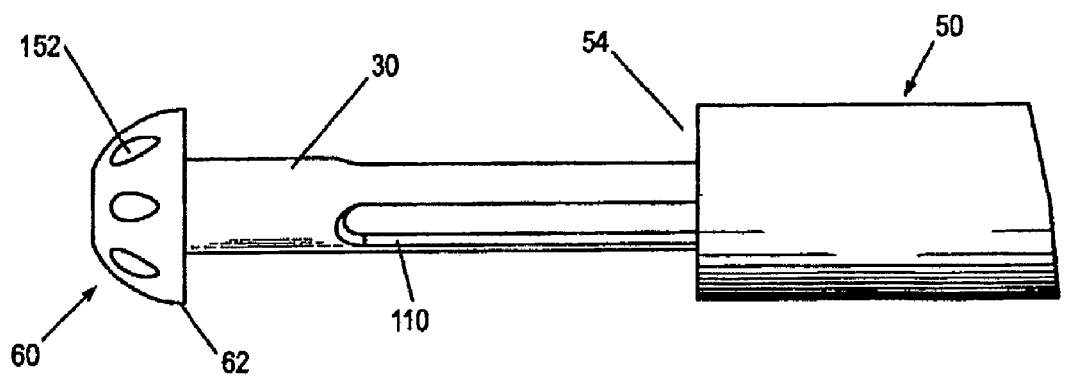
FIG. 21 is a side view of a preferred embodiment of a device for delivering and deploying a radially self-expanding stent featuring an alternative distal tip, as shown in FIG. 20 and visualization windows.

Following in the same spirit of the above-described embodiment, FIG. 19-21 shows an alternative embodiment of device 10 wherein the distal tip 60 has a substantially flat proximal face that can abut the distal face of the outer tubular member 50. Additionally, in either the closed (abutted) or open configurations, instruments can freely pass through the utility channels 55 of the outer tubular member 50 and the utility channels 152, which are formed through distal tip 60 to complement the utility channels 55 of the outer tubular member 50.

In both the above, and alternative embodiments, one or more of the utility channels 55 and 152 themselves may be optical fibers or bundles of optical fibers allowing for direct visualization distal, proximal and through the delivery and deployment device 10. Moreover, the utility grooves 150 may also have internally and/or externally facing optical components. In addition, the inner surfaces 32 and 56 of the inner 30 and outer 50 tubular members (working channels) may themselves comprise optical characteristics and/or be formed of optical material. Therefore, reference throughout, including in the appended claims, to optical capabilities in the these components refers to either inherit capacity of the component material or capacity provided by adaptively introduced optical components or both.

Referring to the functional aspects of the device 10, there is shown in FIG. 1 a deployment apparatus 10 that includes an elongate and flexible outer tubular member 50 constructed of at least one biocompatible thermoplastic elastomer, e.g. such as polyurethane and nylon, typically with an outside diameter 52 in the range of about between 6-9 mm. A central lumen 56 runs the length of the outer tubular member 50. A distal region 54 of the outer tubular member 50 surrounds the stent to be placed (not shown), and maintains the stent in a crimped delivery configuration, against an elastic restoring force of the stent. The stent, when in a normal unrestrained configuration, generally has a diameter (for example, 10-20 mm) substantially larger than the interior diameter 32 of the inner tubular member 30. Typically the expanded stent is larger in diameter than the body lumen in which the stent is fixed, and the restoring force tends to maintain the stent against the tissue wall.

Outer tubular member 50 is mounted at its proximal end to a handle 40. Outer tubular member 50 can be pushed and pulled relative to inner tubular member 30 by hand manipulation of the handle 40 at the proximal end of the outer tubular member 30 and holding the proximal end of the handle 40.

A guidewire 12 is preferably disposed within the interior lumen 32 of an elongate and flexible inner tubular member 30, which can be constructed of materials similar to those employed to form the outer tubular member 50. However, it is preferable that inner tubular member 30 is formed from a more durable material and additionally no guidewire may be necessary. A distal tip 60 is coupled with inner tubular member 30 about the distal end thereof. Also attached to the inner tubular member 30 are a proximal marker 80, at least one medial marker 82 and a distal marker 84. The markers are constructed of a radiopaque material, e.g. platinum iridium, and surround the inner tubular member 30. Markers 80, 82 and 84 are axially spaced apart to mark the length of the stent and to mark the critical deployment distance for that stent length. The markers identify a stent-retaining hub 70 of the inner tubular member 30, more particularly the distal region of the inner tubular member 30 is surrounded by stent 12. Markers 80 and 84 have Exterior Diameters slightly smaller than the interior diameter of outer tubular member 50. The outer tubular member 50 thus functions as a carrier for the stent, with inner tubular member 30 providing a retaining means for radially compressing the stent and maintaining the stent along the stent-retaining hub 70, so long as the outer tubular member 50 surrounds the stent. It should be noted that the markers may be more or fewer in number and may also be formed about the interior diameter 32 of the inner tubular member 30 or alternatively, about the interior diameter 56 or exterior diameter 58 of the outer tubular member 50.

Inner tubular member 30, along its entire length, has an interior lumen 32 open to both the proximal and distal ends of the inner tubular member 30. An axial passage 68 through distal tip 60 continues lumen 32 to allow the guidewire 12 to pass from the proximal handpiece 14 through the distal tip 60.

Handle 40 and outer tubular member 50 are movable relative to inner tubular member 30. More particularly, the handle 40 is moved proximally relative to the stent-retaining hub 70, facilitating the movement of outer tubular member 50 relative to inner tubular member 30 so as to provide a means for controllably withdrawing the outer tubular member 50, relative to the inner tubular member 30, resulting in the release of the stent for radial self-expansion.

The following is a discussion of a preferred embodiment of the device 10 in use but in no way should be construed as limiting with respect to structure and/or method of use.

When the device 10 is used to position the stent, the initial step is to position guidewire 12 within the anatomy of a patient. This can be accomplished with a guide cannula (not illustrated), leaving guidewire 12 in place, with the exchange portion of the guidewire extended proximally beyond the point of entry into the anatomy of the patient. Deployment apparatus 10 is then advanced over the guidewire 12 at the exchange portion, with the guidewire 12 being received into passage 68 of distal tip 60. As device 10 is inserted into the body, the proximal portion of guidewire 12 travels proximally (relative to the device) to the proximal end of guidewire lumen 32.

Once device 10 is positioned, the physician maintains guidewire 12 and inner tubular member 30 substantially fixed with one hand, while moving handle 40 in the proximal direction with the other hand, thus to move outer tubular member 50 proximally relative to inner tubular member 30. As the outer tubular member 50 is retracted, the stent 71 remains substantially fixed relative to inner tubular member 30, and thus radially self-expands. As the handle 40 and correspondingly the outer tubular member 50 are retracted, the handle 40 encounters the safety mechanism 18 for the critical deployment point (see FIG. 4C). The inner tubular member 30, via the handle 40, may have to be rotated to align and insert the stop 20 into the handle 40. When fully inserted, further deployment cannot occur without twisting and snapping the stop the tab 24 portion of the stop 20. Continued retraction of the outer tubular member 50 results in complete deployment of the stent 71.

After deployment, the stent ideally radially self-expands to a diameter greater than the diameter of outer tubular member 50. Accordingly, device 10 can be withdrawn proximally through the stent. However, in the event that the stent does not radially expand fully, distal tip 60 is configured to facilitate removal of deployment apparatus 10 through the lumen of the stent.

Guidewire 12 can be withdrawn as well. The guidewire 12 emerges from the proximal end of the proximal handpiece 14. However, should the medical procedure involve further treatment, e.g., placement of a further stent, the deployment apparatus 10 can be removed without removing the guidewire 12. Device 10 is removed by progressively pulling the device away from the guidewire 12 (which removes the guidewire from within the inner tubular member 30), all while maintaining guidewire 12 in place.

Returning to distal tip 60, as illustrated in FIGS. 4A, 4B and 6, distal tip 60 can have a variety of confirmations, but by way of non-limiting example, distal tip 60 comprises first 62 and second 66 ends having a smaller diameter than the medial region 64 thereof. In a preferred embodiment, each end is conical in shape so as to allow the tip 60 to wedge through an incompletely expanded stent when pulled proximally with respect to the stent. Moreover, the dual conical end design facilitates removal but sufficiently prevents the crimped stent from releasing from the stent-retaining hub 70 and prematurely expanding. Distal tip 60 may alternatively have a flared medial region 64 so as to facilitate retrieval and retraction of a misaligned stent 12.

With respect to additional safety features incorporated in the present device 10, in a preferred embodiment, the device 10 has a deployment safety mechanism 18 that comprises male 46 and female 22 locking members that are brought into functional engagement as the stent is being deployed. Once the stent has reached the critical deployment point, the distal end of the stop 20 is substantially flush with the base 44 of the handle cavity 42 and the female locking members 22 of the stop 20 are in operative communication with the corresponding male locking members 46 formed on the interior surface of the cavity 42 of the handle. When the safety mechanism 18 is engaged as described above, the stent cannot be deployed further without physician intervention. In order to deploy the stent beyond this point, the physician has to rotate the stop 20 to cause the tab 24 to break. Once the tab 24 is broken, the device 10 is in the proceed orientation and deployment may proceed. This safety mechanism is in contrast to locks that merely serve as a stabilizer to prevent movement of the tubes during a procedure.

In a preferred embodiment, the physician will feel a tactile indication that the device 10 can be deployed further. Alternatively, the breaking of the tab may also, or as a substitute to tactile indication, results in an audible indication that further deployment is possible. Additionally, the physician is apprised of the fact that deployment beyond this point is irreversible except for interventional retrieval methods. As discussed earlier, the critical deployment point is preferably about 60% deployment, beyond which retraction is not recommended. As a result, the safety mechanism 18 removes the need to estimate extent of deployment and provides a reliable means of accurately deploying stents. Alternative locking mechanisms may be provided as long as they retain the important characteristic of giving the physician a sensory indication of extent of stent deployment and removes the need to estimate extent of deployment. By way of non-limiting example only, the locking mechanism could comprise a breakable seal, tab/stop lock, diverted channel safety mechanism, etc.

Figure 12:
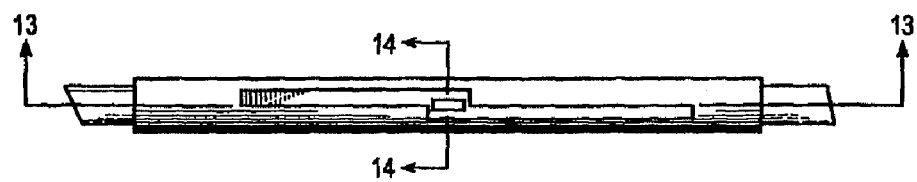
FIG. 12 is a perspective view of a portion of a deployment safety mechanism in accordance with the present invention.

Referring specifically to FIG. 12, a diverted channel safety mechanism is provided generally as 118. In particular, about the stop 20 or as an alternative to the stop 20, a detent 90 is coupled with the hypotube 16. As the hypotube 16 and inner tubular member 30 are advanced distally or, alternatively, the outer tubular member 50 is retracted proximally, the detent 90 comes into contact with the base 44 of the cavity 42 of the handle 40. The handle 40, in this alternative embodiment, defines a substantially Z shaped channel 43 that is essentially a continuation of the cavity 43. The shape of the channel 43 may vary from an L, S, T or other suitable shape for encouraging user intervention. In practice, physician intervention comprises the step of rotating the hypotube 16 such that the detent 90 no longer abuts the base 44 of the handle cavity 42, rather once rotated, the detent 90 is disposed within the channel 43 of the handle 40 allowing free stent deployment. In the furtherance of this safety mechanism 118, it is preferable that the point of detent/base interaction is about approximately the critical deployment point. The principal thrust of this and other safety mechanisms that fall within the scope of this invention is that deployment is limited to a point where the stent and the device are still retractable absent additional user intervention. Beyond this point, the user understands that deployment may not be easily aborted and reversed.

Figure 11:
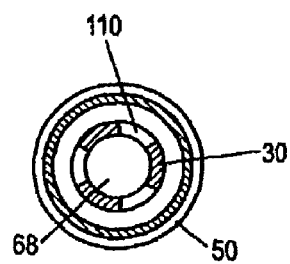
FIG. 11 shows a frontal view of the visualization features along lines 11-11 of FIG. 9.

As an enhancement to facilitate optimal visualization within the workspace, the inner tubular member 30 defines at least one aperture there through to facilitate viewing with an optical instrument. The aperture(s) generally referred to as optical window 110 are preferably beveled, as shown in FIG. 11, to maximize the viewing area available to the optical scope. In a preferred embodiment, as shown in FIG. 15, where there is a plurality of optical windows 110, the optical windows 110 may be offset or staggered so that at different deployment depths, there is an available optical window 110. Moreover, these optical windows 110 are preferably oval, but may be any number of geometrical shapes such as a polygon, spherical, etc.

Figure 13:
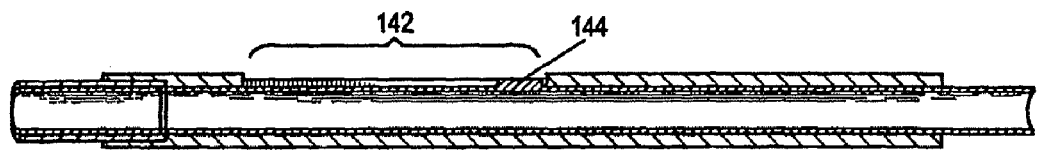
FIG. 13 is a perspective view of the slide cavity of the safety mechanism as shown along lines 13-13 of the device of FIG. 12.
Figure 14:
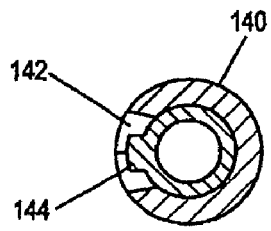
FIG. 14 is a perspective view of a portion of a deployment safety mechanism as shown along lines 14-14 of FIG. 12.

FIGS. 12-14 show a preferred safety mechanism. The principal feature is the requirement of user intervention in order to fully deploy the stent. This insures that stents are not prematurely deployed. It should also be kept in mind that all of the alternative embodiments of the present invention may be provided with varying dimensions depending on the interventional necessity. For example, as discussed above, the device 10 may have longer or shorter overall dimensions depending on the deployment protocol.

It should be kept in mind that certain embodiments of the present invention provide for the deployment of specialized stents to treat one of the most common causes of spontaneous non-traumatic pneumothorax, namely, a pulmonary bleb. In particular, stents specifically designed to treat a pulmonary bleb may be delivered via the present delivery device. The dimensions and spacing of the stent-retaining hub 70 are modified to accommodate the different shape of the stent. Moreover, since the stent has a substantially thimble shape and preferably a self-healing semi-permeable membrane cover, the device 10 does not have the double conical shaped distal tip 60. Rather, radial pressure exerted by the bleb stent against the interior surface 56 of the outer tubular member 50 provides sufficient resistance to keep the stent in place prior to deployment. At the time and location of desired deployment, the outer tubular member 50 can be retracted to fully deploy the stent. Additionally, any of the aforementioned configurations for guidewires and optical instruments would allow for acceptable visualization of the target area.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A device for allowing a user to deploy a stent in an anatomical lumen of a patient, the device comprising:
   a longitudinally extending inner tubular member having distal and proximal ends, the inner tubular member defines a lumen longitudinally extending substantially the distance from the distal end to the proximal end of the inner tubular member and forming a longitudinal expanse there between, the longitudinal expanse forming an aperture there through, and the inner tubular member having a tip coupled with the distal end;
   a longitudinally extending outer tubular member having an exterior and interior diameter, the outer tubular member being longitudinally and axially displaceable relative to the inner tubular member and including at least one longitudinally extending channel formed between the exterior and interior diameter of the outer tubular member;
   a handle configured to displace the outer tubular member and inner tubular member relative to each other in response to user intervention, the handle coupled with the outer tubular member, the handle having first and second ends and the second end including a cavity defined therein;
   a stop disposed substantially about a circumference of the inner tubular member and configured to coaxially engage the cavity within the handle to form a safety mechanism;
   whereby displaceability of the outer tubular member and inner tubular member relative to each other is limited by the safety mechanism to a predetermined threshold absent intervention by the user of the device such that the outer tubular member is configured to partially surround the stent at the predetermined threshold and the stent is not fully deployed when the stop is engaged with the cavity.

2. The device of claim 1, wherein the longitudinally extending channels accommodate utility instruments through a lumen thereof.

3. The device of claim 2, wherein the utility instruments are selected from the group consisting of guidewires, optical devices, syringe systems or combinations thereof.

4. The device of claim 3, wherein the guidewire has optical capabilities.

5. The device of claim 3, wherein the guidewire has ultrasound capabilities.

6. The device of claim 3, wherein the syringe system has capabilities selected from the group consisting of thermotherapy, cryotherapy, electrocautery therapy, photodynamic therapy, chemotherapy or combinations thereof.

7. The device of claim 6, wherein the syringe system is capable of administering a bioactive product.

8. The device of claim 7, wherein the bioactive product is a chemotherapeutic agent.

9. The device of claim 8, wherein the chemotherapeutic agent is selected from the group consisting of DNA-interactive Agents, Antimetabolites, Tubulin-Interactive Agents, Hormonal agents and others such as Asparaginase or Hydroxyurea.

10. The device of claim 9, wherein the Antimetabolites are selected from the group consisting of folate antagonists such as Methotrexate and trimetrexate; pyrimidine
    antagonists, such as Fluorouracil, Fluorodeoxyuridine, CB3717, Azacytidine, Cytarabine; Floxuridine purine antagonists include Mercaptopurine, 6-Thioguanine, Fludarabine, Pentostatin; sugar modified analogs include Cyctrabine, Fludarabine; and ribonucleotide reductase inhibitors include Hydroxyurea.

11. The device of claim 8, wherein the DNA-interactive Agents are selected from the group consisting of alkylating agents, DNA strand-breakage agents, intercalating topoisomerase II inhibitors, and nonintercalating topoisomerase II inhibitors.

12. The device of claim 11, wherein the alkylating agents are selected from the group consisting of Nitrogen mustards, aziridines, nitroso ureas, platinum complexes, bioreductive alkylator, DNA strand breaking agents, Intercalators and nonintercalators.

13. The device of claim 9, wherein the bioactive product comprises a hormonal agent.

14. The device of claim 13, wherein the hormonal agent is selected from the group consisting of estrogens, conjugated estrogens; progestins; and androgens.

15. The device of claim 9, wherein the bioactive product comprises an anti-hormonal agent.

16. The device of claim 15, wherein the anti-hormonal agent is selected from the group consisting of antiestrogenic, antiandrogen agents, and antiadrenal agents.

17. The device of claim 1, further comprising a distal tip having an interior and an exterior surface and distal and proximal ends.

18. The device of claim 17, wherein the distal tip further comprises a light source.

19. The device of claim 18, wherein the distal tip further comprises a lens.

20. The device of claim 17, wherein the distal tip further comprises utility grooves formed along the exterior surface thereof, which extend substantially between the distal and proximal ends thereof 21. The device of claim 17, wherein the distal tip defines a plurality of apertures formed there through.

22. The device of claim 1, wherein the user intervention comprises displacing the outer tubular member axially relative to the inner tubular member.

23. The device of claim 22, wherein an audible indication follows the user intervention.

24. The device of claim 22, wherein a tactile indication follows the user intervention.

25. The device of claim 22, wherein the outer tubular member when moved longitudinally relative to the inner tubular member in a proximal direction away from the selected location, releases the stent for radial self-expansion.

26. The device of claim 1, wherein the predetermined threshold is about between 10% and 90% deployment.

27. The device of claim 26, wherein the predetermined threshold is about 60% deployment.

28. The device of claim 1, wherein a guidewire is introduced through a portion of the exterior diameter of the outer tubular member.

29. The device of claim 1, wherein the at least one longitudinally extending channel of the outer tubular member is configured to receive an optical scope.

30. The device of claim 1, wherein the outer tubular member is clear.

31. The device of claim 1, wherein there is at least one marker coupled with a portion of the inner tubular member.

32. The device of claim 1, wherein there is at least one marker coupled with a portion of the outer tubular member.

33. The device of claim 1, wherein the inner tubular member is of a material that is kink resistant.

34. The device of claim 1 or 33, wherein the outer tubular member is kink resistant.

35. The device of claim 1, wherein the distal tip has first, medial and second sections, the first and second sections having exterior diameters that are less than that of the medial section.

36. The device of claim 1, wherein a portion of the inner tubular member about the proximal end further comprises a stent carrier adapted to carry a radially self-expanding stent in a radially contracted state.

37. The device of claim 36, further including a radially self-expanding stent carried by the stent carrier, extended along and surrounding at least part of the distal end region, and surrounded by a portion of the outer tubular member and thereby maintained in the radially contracted state.

38. The device of claim 1, further comprising a hypotube having a first end and a second end, wherein the stop is formed on the hypotube between the first and second ends.

39. The device of claim 38, further comprising at least one tab formed on the stop when the stop is molded on the hypotube, wherein the tab is configured to be broken during user intervention.

40. The device of claim 1, wherein the stop is spaced distally from the proximal end of the inner tubular member.

41. A device for allowing a user to deploy a stent in an anatomical lumen of a patient, the device comprising:

a longitudinally extending inner tubular member having distal and proximal ends, the inner tubular member defines a lumen longitudinally extending substantially the distance from the distal end to the proximal end of the inner tubular member and forming a longitudinal expanse there between, the longitudinal expanse forming an aperture there through, and the inner tubular member having a distal tip coupled with the distal end, wherein the inner tubular member, about the distal end and proximal the distal tip, further comprises a stent carrier adapted to underlie and carry a stent in a radially contracted state, the lumen of the inner tubular member configured to receive an optical scope such that the scope is capable of extending through the lumen, through a stent disposed on the stent carrier, and distally of the distal tip, wherein the inner tubular member comprises at least one optical window defined therein and configured to facilitate visualization therethrough by the optical scope;

a longitudinally extending outer tubular member having an exterior and interior diameter, the outer tubular member being longitudinally and axially displaceable relative to the inner tubular member;

a handle, coupled with a portion of the outer tubular member;

a stop disposed about the inner tubular member and configured to engage the handle to form a safety mechanism; and a hypotube having a first end and a second end, wherein the stop is formed on the hypotube between the first and second ends, whereby the extent of displaceability of the outer tubular member and inner tubular member relative to each other is limited by the safety mechanism to a predetermined threshold absent intervention by the user of the device such that the degree of stent deployment is limited by the safety mechanism absent intervention by the user and the outer tubular member is configured to partially surround the stent at the predetermined threshold.

42. The device of claim 41, wherein the outer tubular member defines longitudinally extending channels formed between the exterior and interior diameter of the outer tubular member, and wherein the longitudinally extending channels accommodate utility instruments through a lumen thereof.

43. The device of claim 42, wherein the utility instruments are selected from the group consisting of guidewires, optical devices, syringe systems or combinations thereof.

44. The device of claim 43, wherein the syringe system has capabilities selected from the group consisting of thermotherapy, cryotherapy, photodynamic therapy, chemotherapy or combinations thereof.

45. The device of claim 43, wherein the guidewire has optical capabilities.

46. The device of claim 43, wherein the guidewire has ultrasound capabilities.

47. The device of claim 44, wherein the syringe system is capable of administering a bioactive product.

48. The device of claim 47, wherein the bioactive product comprises a hormonal agent.

49. The device of claim 48, wherein the hormonal agent is selected from the group consisting of estrogens, conjugated estrogens; progestins; and androgens.

50. The device of claim 47, wherein the bioactive product comprises an anti-hormonal agent.

51. The device of claim 50, wherein the anti-hormonal agent is selected from the group consisting of antiestrogenic, antiandrogen agents, and antiadrenal agents.

52. The device of claim 47, wherein the bioactive product is a chemotherapeutic agent.

53. The device of claim 52, wherein the chemotherapeutic agent is selected from the group consisting of DNA-interactive Agents, Antimetabolites, Tubulin-Interactive Agents, Hormonal agents and others such as Asparaginase or Hydroxyurea.

54. The device of claim 53, wherein the Antimetabolites are selected from the group consisting of folate antagonists such as Methotrexate and trimetrexate; pyrimidine antagonists, such as Fluorouracil, Fluorodeoxyuridine, CB3717, Azacytidine, Cytarabine; Floxuridine purine antagonists include Mercaptopurine, 6-Thioguanine, Fludarabine, Pentostatin; sugar modified analogs include Cyctrabine, Fludarabine; and ribonucleotide reductase inhibitors include Hydroxyurea.

55. The device of claim 52, wherein the DNA-interactive Agents are selected from the group consisting of alkylating agents, DNA strand-breakage agents, intercalating topoisomerase II inhibitors, and nonintercalating topoisomerase II inhibitors.

56. The device of claim 55, wherein the alkylating agents are selected from the group consisting of Nitrogen mustards, aziridines, nitroso ureas, platinum complexes, bioreductive alkylator, DNA strand breaking agents, Intercalators and non-intercalators.

57. The device of claim 42, wherein the longitudinally extending channels of the outer tubular member are configured to receive an optical scope.

58. The device of claim 41, further comprising a distal tip having an interior and an exterior surface and distal and proximal ends.

59. The device of claim 58, wherein the distal tip further comprises a light source.

60. The device of claim 58, wherein the distal tip further comprises a lens.

61. The device of claim 58, wherein the distal tip further comprises utility grooves formed along the exterior surface thereof, which extend substantially between the distal and proximal ends thereof.

62. The device of claim 58, wherein the distal tip defines a plurality of apertures formed there through.

63. The device of claim 41, wherein the user intervention comprises displacing the outer tubular member axially relative to the inner tubular member.

64. The device of claim 63, wherein an audible indication follows the user intervention.

65. The device of claim 63, wherein a tactile indication follows the user intervention.

66. The device of claim 63, further comprising at least one tab formed on the stop, which serves as the audible indication when broken during user intervention.

67. The device of claim 63, wherein the outer tubular member when moved longitudinally relative to the inner tubular member in a proximal direction away from the selected location, releases the stent for radial self-expansion.

68. The device of claim 41, wherein the predetermined threshold is about between 10% and 90% deployment.

69. The device of claim 68, wherein the predetermined threshold is about 60% deployment.

70. The device of claim 41, wherein a guidewire is introduced through a portion of the exterior diameter of the outer tubular member.

71. The device of claim 41, wherein the outer tubular member is clear.

72. The device of claim 41, wherein there is at least one marker coupled with a portion of the inner tubular member.

73. The device of claim 41, wherein there is at least one marker coupled with a portion of the outer tubular member.

74. The device of claim 41, wherein the inner tubular member is of a material that is kink resistant.

75. The device of claim 41, wherein the outer tubular member is kink resistant.

76. The device of claim 41, wherein the distal tip has first, medial and second sections, the first and second sections having Exterior Diameters that are less than that of the medial section.

77. The device of claim 41, wherein a portion of the inner tubular member about the proximal end further comprises a stent carrier adapted to carry a radially self-expanding stent in a radially contracted state.

78. The device of claim 77, further including a radially self-expanding stent carried by the stent carrier, extended along and surrounding at least part of the distal end region, and surrounded by a portion of the outer tubular member and thereby maintained in the radially contracted state.

79. A device for allowing a user to deploy a stent in an anatomical lumen of a patient, the device comprising:
  a longitudinally extending inner tubular member having distal and proximal ends, the inner tubular member defines a lumen longitudinally extending substantially the distance from the distal end to the proximal end of the inner tubular member and forming a longitudinal expanse there between, the longitudinal expanse forming an aperture there through, and the inner tubular member having a tip coupled with the distal end, wherein the tip comprises a plurality of apertures defined therethrough, the inner tubular member further comprising a stent carrier adapted to carry a radially self-expanding stent in a radially contracted state proximate to the distal end and proximal the distal tip; and
  a longitudinally extending outer tubular member having proximal and distal ends and an exterior and interior diameter, the outer tubular member being longitudinally and axially displaceable relative to the inner tubular member, wherein the outer tubular member defines longitudinally extending channels formed between the exterior and interior diameter thereof, wherein the longitudinally extending channels are configured to align with a respective aperture defined in the distal tip, wherein an exterior diameter of a proximal end of the distal tip is substantially the same as the exterior diameter of the distal end of the outer tubular member, and wherein the exterior diameter of the outer tubular member is substantially the same between its proximal and distal ends.

80. The device of claim 79, further including a radially self-expanding stent carried by the stent carrier, extended along and surrounding at least part of the distal end region, and surrounded by a portion of the outer tubular member and thereby maintained in the radially contracted state.

81. The device of claim 80, wherein the outer tubular member when moved longitudinally relative to the inner tubular member in a proximal direction away from the selected location, releases the stent for radial self-expansion.

82. The device of claim 79, wherein each of the longitudinally extending channels are configured to accommodate at least one utility instrument through a lumen thereof.

83. The device of claim 82, wherein the utility instruments are selected from the group consisting of guidewires, optical devices, syringe systems or combinations thereof.

84. The device of claim 83, wherein the guidewire has optical capabilities.

85. The device of claim 83, wherein the guidewire has ultrasound capabilities.

86. The device of claim 83, wherein the syringe system has capabilities selected from the group consisting of thermotherapy, cryotherapy, electrocautery therapy, photodynamic therapy, chemotherapy or combinations thereof.

87. The device of claim 86, wherein the syringe system is capable of administering a bioactive product.

88. The device of claim 87, wherein the bioactive product is a chemotherapeutic agent.

89. The device of claim 88, wherein the DNA-interactive Agents are selected from the group consisting of alkylating agents, DNA strand-breakage agents, intercalating topoisomerase II inhibitors, and nonintercalating topoisomerase II inhibitors.

90. The device of claim 89, wherein the alkylating agents are selected from the group consisting of Nitrogen mustards, aziridines, nitroso ureas platinum complexes, bioreductive alkylator, DNA strand breaking agents, Intercalators and non-intercalators.

91. The device of claim 88, wherein the chemotherapeutic agent is selected from the group consisting of DNA-interactive Agents, Antimetabolites, Tubulin-Interactive Agents, Hormonal agents and others such as Asparaginase or Hydroxyurea.

92. The device of claim 91, wherein the Antimetabolites are selected from the group consisting of folate antagonists such as Methotrexate and trimetrexate; pyrimidine antagonists, such as Fluorouracil, Fluorodeoxyuridine, CB3717, Azacytidine, Cytarabine; Floxuridine purine antagonists include Mercaptopurine, 6-Thioguanine, Fludarabine, Pentostatin; sugar modified analogs include Cyctrabine, Fludorabine; and ribonucleotide reductase inhibitors include Hydroxyurea.

93. The device of claim 91, wherein the bioactive product comprises a hormonal agent.

94. The device of claim 93, wherein the hormonal agent is selected from the group consisting of estrogens, conjugated estrogens; progestins; and androgens.

95. The device of claim 91, wherein the bioactive product comprises on anti-hormonal agent.

96. The device of claim 95, wherein the anti-hormonal agent is selected from the group consisting of antiestrogenic, antiandrogen agents, and antiadrenal agents.

97. The device of claim 79, wherein the distal tip comprises an interior and an exterior surface and distal and proximal ends.

98. The device of claim 97, wherein the distal tip comprises a lumen extending between the proximal and distal ends of the distal tip that is configured to align with the lumen of the inner tubular member.

99. The device of claim 79, wherein a guidewire is introduced through a portion of the exterior diameter of the outer tubular member.

100. The device of claim 79, wherein the longitudinally extending channels of the outer tubular member is configured to receive an optical scope.

101. The device of claim 79, wherein the outer tubular member is clear.

102. The device of claim 79, wherein there is at least one marker coupled with a portion of the inner tubular member.

103. The device of claim 79, wherein there is at least one marker coupled with a portion of the outer tubular member.

104. The device of claim 79, wherein the inner tubular member is of a material that is kink resistant.

105. The device of claim 104, wherein the outer tubular member is kink resistant.

106. A device for allowing a user to deploy a stent in an anatomical lumen of a patient, the device comprising:

a longitudinally extending inner tubular member having distal and proximal ends, the inner tubular member defines a lumen longitudinally extending substantially the distance from the distal end to the proximal end of the inner tubular member and forming a longitudinal expanse there between, the longitudinal expanse forming an aperture there through, and the inner tubular member having a tip coupled with the distal end, the lumen of the inner tubular member configured to receive an optical scope such that the optical scope is capable of extending through the lumen and distally of the tip, wherein the inner tubular member comprises at least one optical window defined therein and configured to facilitate visualization therethrough by the optical scope;

a longitudinally extending outer tubular member being longitudinally and axially displaceable relative to the inner tubular member;

a handle configured to displace the outer tubular member and inner tubular member relative to each other in response to user intervention, the handle coupled to the outer tubular member, the handle having first and second ends, wherein the second end of the handle includes a cavity defined circumferentially therein and about the outer tubular member;

a stop disposed substantially about a circumference of the inner tubular member and configured to engage the cavity within the handle to form a safety mechanism;

whereby displaceability of the outer tubular member and inner tubular member relative to each other is limited by the safety mechanism to a predetermined threshold absent intervention by the user of the device such that the outer tubular member is configured to partially surround the stent at the predetermined threshold and the stent is not fully deployed when the stop is engaged with the cavity.

107. A device for allowing a user to deploy a stent in an anatomical lumen of a patient, the device comprising:

a longitudinally extending inner tubular member having distal and proximal ends, the inner tubular member defines a lumen longitudinally extending substantially the distance from the distal end to the proximal end of the inner tubular member and forming a longitudinal expanse there between, the longitudinal expanse forming an aperture there through, and the inner tubular member having a tip coupled with the distal end, the lumen of the inner tubular member configured to receive an optical scope such that the optical scope is capable of extending through the lumen and distally of the tip, wherein the inner tubular member comprises at least one optical window defined therein and configured to facilitate visualization therethrough by the optical scope;

a longitudinally extending outer tubular member being longitudinally and axially displaceable relative to the inner tubular member;

a handle configured to displace the outer tubular member and inner tubular member relative to each other in response to user intervention, the handle coupled to the outer tubular member, the handle having proximal and distal ends, wherein the proximal end of the handle includes a cavity defined therein;

a stop coupled to the inner tubular member and disposed substantially about a circumference thereof such that the stop is configured to engage the cavity within the handle when the outer tubular member is displaced relative to the inner tubular member to a predetermined threshold;

whereby displaceability of the outer tubular member and inner tubular member relative to each other is limited to the predetermined threshold when the stop is in engagement with the cavity and such that complete deployment of the stent is limited absent intervention by the user and the outer tubular member is configured to partially surround the stent at the predetermined threshold.

108. A device for allowing a user to deploy a stent in an anatomical lumen of a patient, the device comprising:

a longitudinally extending inner tubular member having distal and proximal ends, the inner tubular member defines a lumen longitudinally extending substantially the distance from the distal end to the proximal end of the inner tubular member and forming a longitudinal expanse there between, the longitudinal expanse forming an aperture there through, and the inner tubular member having a tip coupled with the distal end, the lumen of the inner tubular member configured to receive an optical scope such that the optical scope is capable of extending through the lumen and distally of the tip, wherein the inner tubular member comprises at least one optical window defined therein and configured to facilitate visualization therethrough by the optical scope;

a longitudinally extending outer tubular member being longitudinally and axially displaceable relative to the inner tubular member;

a handle configured to displace the outer tubular member and inner tubular member relative to each other in response to user intervention, the handle coupled to the outer tubular member, the handle having proximal and distal ends, wherein the proximal end of the handle includes a cavity defined therein;

a stop disposed substantially about a circumference of the inner tubular member and positioned proximally of the cavity such that the stop is configured to engage the cavity when the handle is displaced in a proximal direction to a predetermined threshold;

whereby displaceability of the outer tubular member and inner tubular member relative to each other is limited by engagement of the stop within the cavity to the predetermined threshold absent intervention by the user of the device such that the outer tubular member is configured to partially surround the stent at the predetermined threshold and the stent is not fully deployed when the stop is engaged with the cavity.

* * * * *

UNITED STATES PATENT AND TRADEMARK OFFICE
CERTIFICATE OF CORRECTION

PATENT NO. : 7,637,934 B2 Page 1 of 1
APPLICATION NO. : 10/404197
DATED : December 29, 2009
INVENTOR(S) : Mangiardi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 267 days.

Signed and Sealed this

Ninth Day of November, 2010

David J. Kappos
*Director of the United States Patent and Trademark Office*